(12) United States Patent
Saha et al.

(10) Patent No.: US 10,485,796 B2
(45) Date of Patent: *Nov. 26, 2019

(54) LPT-723 AND IMMUNE CHECKPOINT INHIBITOR COMBINATIONS AND METHODS OF TREATMENT

(71) Applicant: BIOMED VALLEY DISCOVERIES, INC., Kansas City, MO (US)

(72) Inventors: Saurabh Saha, Wellesley Hills, MA (US); Linping Zhang, Lexington, MA (US); Xiaoyan Michelle Zhang, Lexington, MA (US)

(73) Assignee: BIOMED VALLEY DISCOVERIES, INC., Kansas City, MO (US)

(*) Notice: Subject to any disclaimer, the term of this patent is extended or adjusted under 35 U.S.C. 154(b) by 53 days.

This patent is subject to a terminal disclaimer.

(21) Appl. No.: 15/809,759

(22) Filed: Nov. 10, 2017

(65) Prior Publication Data

US 2018/0117020 A1  May 3, 2018

Related U.S. Application Data

(63) Continuation of application No. 15/195,723, filed on Jun. 28, 2016, now Pat. No. 9,861,621.

(60) Provisional application No. 62/186,157, filed on Jun. 29, 2015.

(51) Int. Cl.

| | | |
|---|---|---|
| *A61K 31/444* | (2006.01) | |
| *C07K 16/28* | (2006.01) | |
| *A61K 39/395* | (2006.01) | |
| *A61K 45/06* | (2006.01) | |
| *A61P 35/00* | (2006.01) | |
| *C07D 401/14* | (2006.01) | |
| *A61K 39/00* | (2006.01) | |

(52) U.S. Cl.
CPC ........ *A61K 31/444* (2013.01); *A61K 39/3955* (2013.01); *A61K 39/39558* (2013.01); *A61K 45/06* (2013.01); *A61P 35/00* (2018.01); *C07K 16/2818* (2013.01); *A61K 2039/507* (2013.01); *C07K 2317/76* (2013.01)

(58) Field of Classification Search
CPC ......................... C07D 401/14; A61K 39/3955
USPC ....................................................... 514/333
See application file for complete search history.

(56) References Cited

U.S. PATENT DOCUMENTS

| | | | |
|---|---|---|---|
| 9,861,621 B2* | 1/2018 | Saha ................ | A61K 39/3955 |
| 2013/0309250 A1 | 11/2013 | Cogswell et al. | |
| 2017/0037132 A1 | 2/2017 | Manekas et al. | |
| 2017/0037133 A1 | 2/2017 | Fiedler et al. | |
| 2017/0065716 A1 | 3/2017 | Brooks et al. | |
| 2017/0129911 A1 | 5/2017 | Lippard et al. | |
| 2017/0130271 A1 | 5/2017 | Wong | |

FOREIGN PATENT DOCUMENTS

CA          2925601 A1      4/2015

OTHER PUBLICATIONS

International Search Report and Written Opinion for PCT/US2016/039885.
Brahmer Jr, et al. Safety and activity of anti-PD-L1 antibody in patients with advanced cancer. N. Engl J Med. Jun. 28, 2012;366(26):2455-65.
Bronte V, et al. Identification of a CD11b(+)/Gr-1(+)/CD31(+) myeloid progenitor capable of activating or suppressing CD8(+) T cells. Blood. Dec. 1, 2000;96(12):3838-46.
Bunt SK, et al. Inflammation induces myeloid-derived suppressor cells that facilitate tumor progression. J Immunol. Jan. 1, 2006;176(1):284-90.
Cleary JM, Shapiro GI. Development of phosphoinositide-3 kinase pathway inhibitors for advanced cancer. Curr Oncol Rep. Mar. 2010;12(2):87-94.
Du R, et al. HIF1alpha induces the recruitment of bone marrow-derived vascular modulatory cells to regulate tumor angiogenesis and invasion. Cancer Cell. Mar. 2008; 13(3):206-20.
Grivennikov SI, et al. Immunity, inflammation, and cancer. Cell. Mar. 19, 2010;140(6):883-99.
Hodi FS, et al. Improved survival with ipilimumab in patients with metastatic melanoma. N Engl J Med. Aug. 19, 2010;363(8):711-23.
Kim K, et al. Eradication of metastatic mouse cancers resistant to immune checkpoint blockade by suppression of myeloid-derived cells. Proc Natl Acad Sci U S A. Aug. 12, 2014;111(32):11774-9.

(Continued)

Primary Examiner — Raymond J Henley, III
(74) Attorney, Agent, or Firm — Bryan Cave Leighton Paisner LLP

(57) ABSTRACT

The present invention provides, inter alia, a composition containing a compound of formula (I):

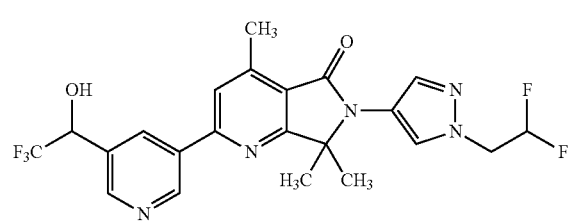

or a pharmaceutically acceptable salt thereof, optionally, in combination with at least one immune checkpoint inhibitor compound. Kits containing the composition, and methods of using the composition for ameliorating or treating the effects of a disease such as a cancer, in a subject, are also provided herein.

14 Claims, 23 Drawing Sheets
(23 of 23 Drawing Sheet(s) Filed in Color)
Specification includes a Sequence Listing.

(56) References Cited

OTHER PUBLICATIONS

Kim S, et al. Carcinoma-produced factors activate myeloid cells through TLR2 to stimulate metastasis. Nature. Jan. 1, 2009;457(7225)102-6.
Korman AJ, et al. Checkpoint blockade in cancer immunotherapy. Adv Immunol. 2006;90:297-339.
Lin EY, et al. Macrophages regulate the angiogenic switch in a mouse model of breast cancer. Cancer Res. Dec. 1, 2006;66(23):11238-46.
Maron DM, Ames BN. Revised methods for the *Salmonella* mutagenicity test. Mutat Res. May 1983;113(3-4)173-215.
McCann J, et al. Detection of carcinogens as mutagens in the *Salmonella*/microsome test: assay of 300 chemicals. Proc Natl Acad Sci U S A. Dec. 1975;72(12):5135-9.
Nagaraj S, et al. Reciprocal relationship between myeloid-derived suppressor cells and T cells. J Immunol. Jul. 1, 2013;191(1):17-23.
Pardoll DM. The blockade of immune checkpoints in cancer immunotherapy. Nat Rev Cancer. Mar. 22, 2012;12(4):252-64.
Schmid MC, et al. Receptor tyrosine kinases and TLR/IL1Rs unexpectedly activate myeloid cell PI3kγ, a single convergent point promoting tumor inflammation and progression. Cancer Cell. Jun. 14, 2011;19(6):715-27.
Talmadge JE, Gabrilovich DI. History of myeloid-derived suppressor cells. Nat Rev Cancer. Oct. 2013;13(10):139-52.
Topalian SL, et al. Safety, activity, and immune correlates of anti-Pd-1 antibody in cancer. N Engl J Med. Jun. 28, 2012;366(26):2443-54.
Wolchok JD, et al. Nivolumab plus ipilimumab in advanced melanoma. N Engl J Med. Jul. 11, 2013;369(2):122-33.

\* cited by examiner

LPT-723 AND IMMUNE CHECKPOINT INHIBITOR COMBINATIONS AND METHODS OF TREATMENT

CROSS-REFERENCE TO RELATED APPLICATIONS

The present application is a continuation of U.S. patent application Ser. No. 15/195,723, filed Jun. 28, 2016, now U.S. Pat. No. 9,861,621, issued Jan. 9, 2018, which claims benefit to U.S. Provisional Application No. 62/186,157, filed Jun. 29, 2015. The entire contents of the above patent documents are incorporated by reference as if recited in full herein.

INCORPORATION BY REFERENCE OF SEQUENCE LISTING

This application contains references to amino acids and/or nucleic acid sequences that have been filed concurrently herewith as sequence listing text file "0563241.txt", file size of 5 KB, created on Nov. 10, 2017. The aforementioned sequence listing is hereby incorporated by reference in its entirety pursuant to 37 C.F.R. § 1.52(e)(5).

FIELD OF THE INVENTION

The present disclosure relates generally to fields of cancer and cancer therapy. More specifically, the present disclosure relates to compositions and methods comprising combinations of PI3Kγ inhibitors and at least one immune checkpoint inhibitor for the treatment of cancer.

BACKGROUND OF THE INVENTION

There is a well-known link between cancer and inflammation. Chronic inflammatory diseases are known to increase risk for developing tumors, and tumors provoke multiple inflammatory responses in order to avoid immune system detection and destruction (Pardoll, 2012; Grivennikov et al., 2010). Cancers are able to exploit regulatory immune system mechanisms, promoting angiogenesis, immunosuppression, and metastasis (Du et al., 2008; Lin et al., 2006; Bronte et al., 2000; Bunt et al., 2006; Kim et al., 2009). These regulatory mechanisms include the activation of myeloid-derived suppressor cells (MDSCs) and immune checkpoint pathways (Korman et al., 2006; Nagaraj et al., 2013; Talmadge and Gabrilovich, 2013).

The disruption of immune checkpoints including programmed cell death-1 (PD-1) and cytotoxic T-lymphocyte-associated antigen-4 (CTLA-4) using antibodies to these receptors has shown promising responses in a subset of patients in recent clinical trials (Hodi et al., 2010; Topalian et al., 2012; Brahmer et al., 2012; Wolchok et al., 2013). However, the majority of patients and tumor types in these trials remain unresponsive to this immunotherapy. A study by Kim et al. (2014) indicated that elevated levels of MDSCs may interfere with checkpoint inhibitor treatment by directly inhibiting the function of CD8+ T cells. Previously it was reported that blocking the PI3-kinase (PI3K) isoform p110γ can inhibit tumor inflammation, growth and metastasis by suppressing MDSCs in a model of spontaneous breast cancer (Schmid, 2011).

One report provides evidence of synergy between a pan-PI3K inhibitor and immune checkpoint blockers to PD1/CTLA4 (Kim et al., 2014). That report demonstrated that reduction in MDSCs via PI3K inhibition contributes to synergy with checkpoint blockade in syngeneic mouse breast and colon tumor models. Pan-PI3K inhibitors have been recently tested in clinical trials, but they broadly inhibit all PI3K isorforms and have been shown to have many deleterious side effects (Cleary and Shapiro, 2010).

In view of the foregoing, there is a need for the development of new and better compositions for reducing MDSCs during immune checkpoint blockade. The present invention is directing to meeting these and other needs.

SUMMARY OF THE INVENTION

Not wishing to be bound by any particular theory, it is believed that pan-PI3K molecules reduce MDSCs through disruption of PI3Kγ isoform signaling. PI3Kγ inhibitors are able to block tumor growth by inhibiting tumor inflammation and angiogenesis without directly affecting tumor cells (Schmid et al., 2011). In the present invention, a selective PI3Kγ inhibitor is combined with immune checkpoint inhibitors and produces a synergistic anti-tumor effect.

Thus, the present invention provides a method for treating or ameliorating the effects of a disorder in a subject comprising administering to the subject an effective amount of a first agent, which is a compound of formula (I):

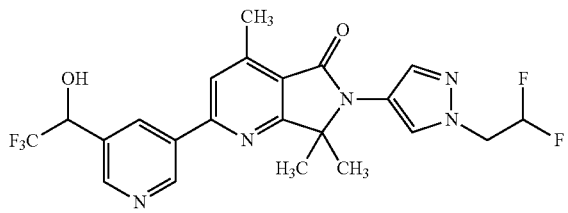 [SMILES: Cc1cc(-c2cncc(C(O)C(F)(F)F)c2)nc2c1C(=O)N(c1cnn(CC(F)F)c1)C2(C)C]

or a pharmaceutically acceptable salt thereof and a second agent, which is an immune checkpoint inhibitor.

The present invention also provides a method for treating or ameliorating the effects of a cancer in a subject comprising administering to the subject an effective amount of a compound of formula (I):

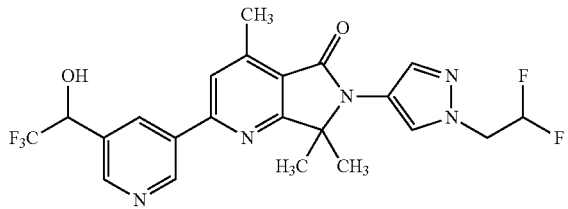

or a pharmaceutically acceptable salt thereof.

The present invention also provides a method for modulating a stromal microenvironment of a cancer comprising contacting the stromal microenvironment of the cancer with a compound of formula (I):

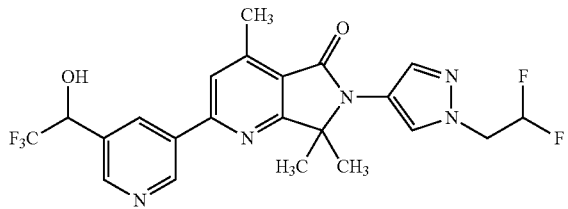

or a pharmaceutically acceptable salt.

The present invention also provides a composition for treating or ameliorating the effects of a disorder in a subject, the composition comprising a first agent, which is a compound of formula (I):

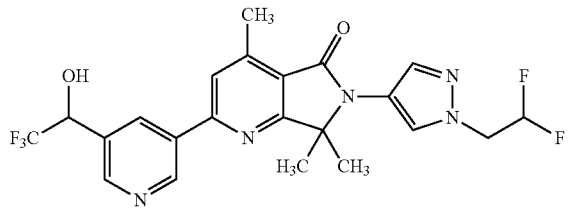 [SMILES: Cc1cc(-c2cncc(C(O)C(F)(F)F)c2)nc2c1C(=O)N(c1cnn(CC(F)F)c1)C2(C)C]

or a pharmaceutically acceptable salt thereof and a second agent, which is an immune checkpoint inhibitor.

The present invention also provides a kit comprising a first agent, which is a compound of formula (I):

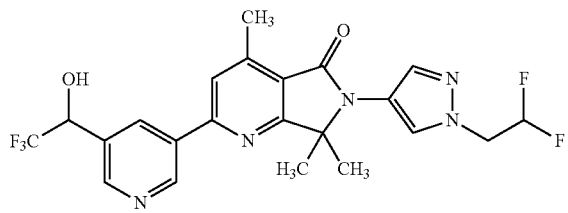 [SMILES: Cc1cc(-c2cncc(C(O)C(F)(F)F)c2)nc2c1C(=O)N(c1cnn(CC(F)F)c1)C2(C)C]

or a pharmaceutically acceptable salt thereof and a second agent, which is an immune checkpoint inhibitor, together with instructions for their use.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

Figure 15:
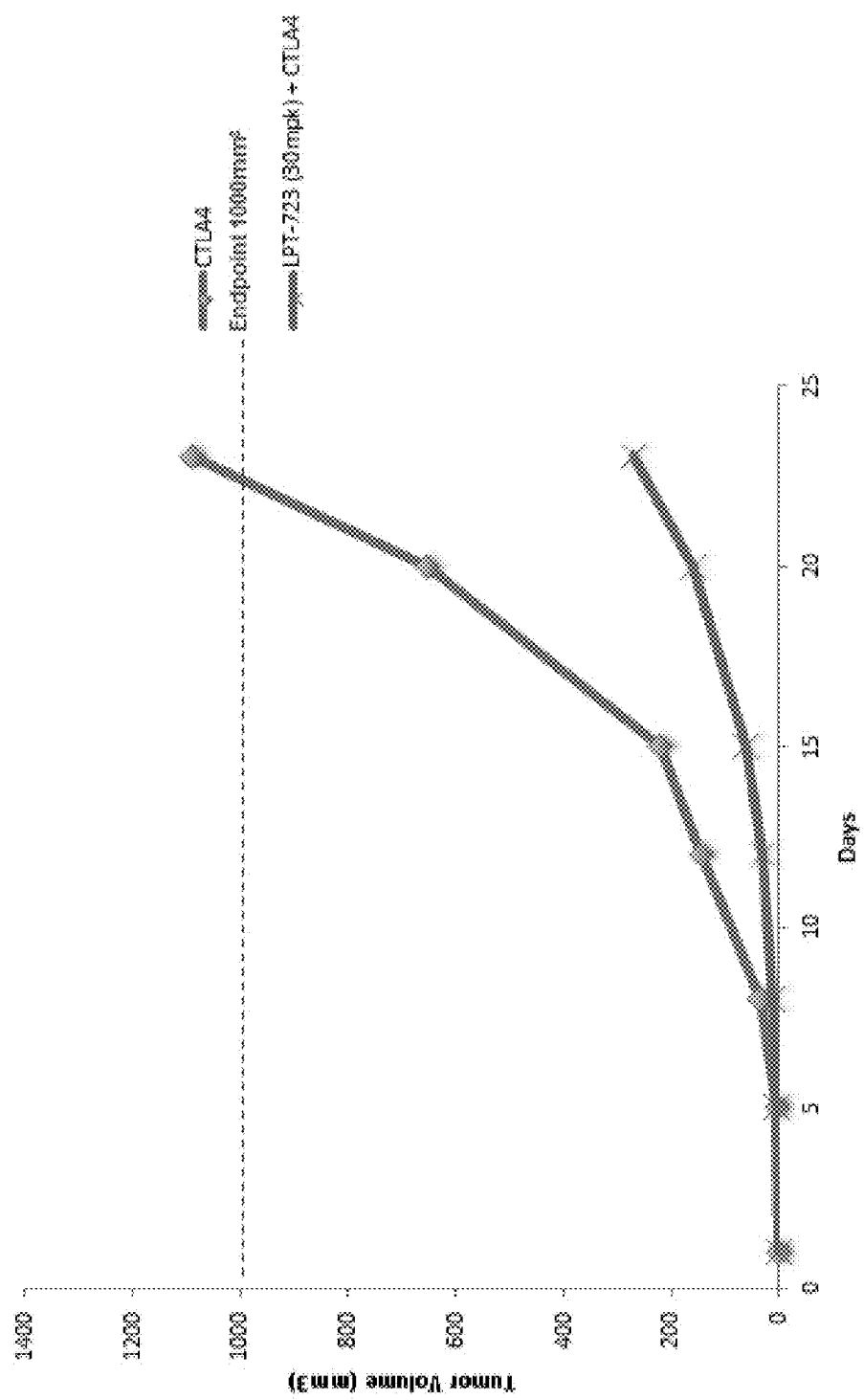

FIG. 15 is a graph of median tumor volume in the LLC syngeneic mouse model. LPT-723 (30 mg/kg twice daily starting day 2) combined with anti-CTLA-4 significantly inhibited tumor growth in comparison with anti-CTLA-4 alone. N=10 animals per group.

Figure 16A:
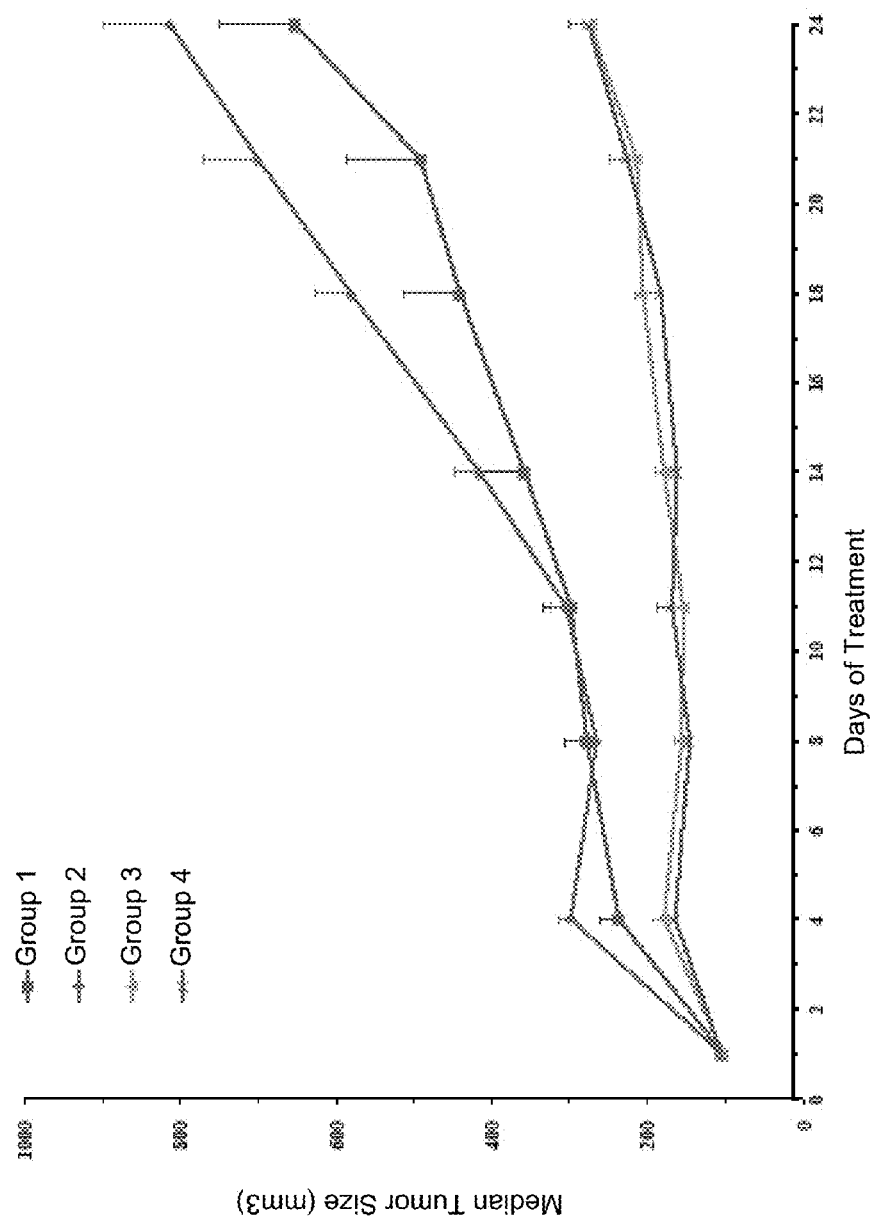
Figure 16B:
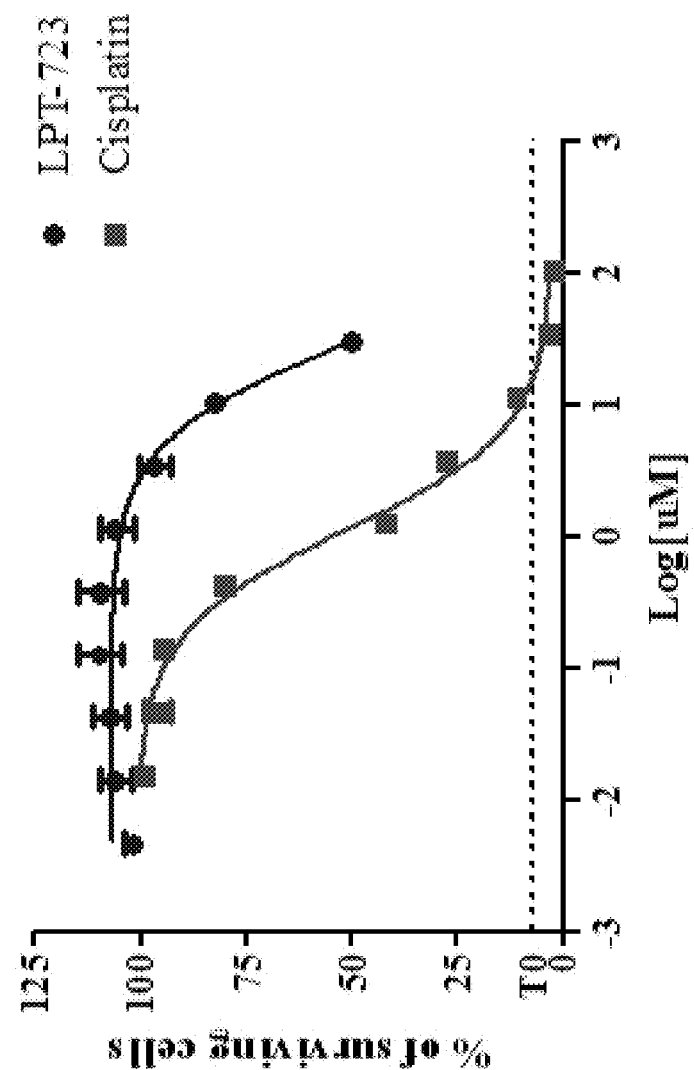

FIG. 16A-FIG. 16B show the effects of LPT-723 in a Pan02 pancreatic cancer syngeneic mouse model. FIG. 16A is a graph showing median tumor volume over 24 days for LPT-723 monotherapy and combination therapy with anti-PD-1. Group 1 (vehicle) received phosphate buffered saline (PBS) twice weekly i.p. and 0.2% MC/1% SLS in deionized (DI) water twice daily orally. Group 2 received anti-PD-1 at 10 mg/kg twice weekly i.p. Group 3 received LPT-723 at 30 mg/kg twice daily by mouth. Group 4 received LPT-723 and anti-PD-1 at the aforementioned doses. There were no significant changes in body weights. N=10 animals per group. FIG. 16B shows an in vitro cell viability assay showing that LPT-723 does not directly kill Pan02 cells ($IC_{50}$=26.57 μM).

Figure 17A:
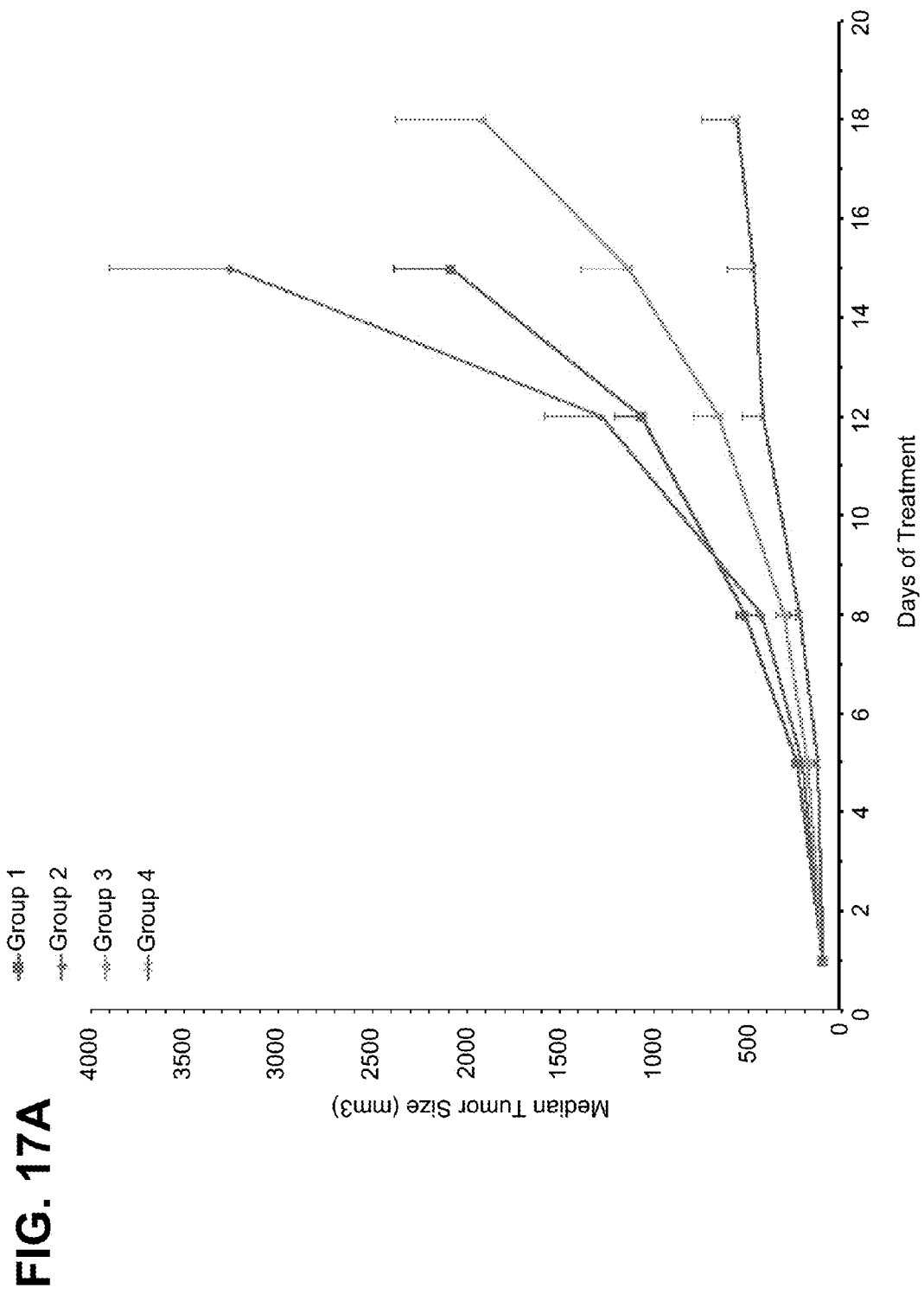
Figure 17B:
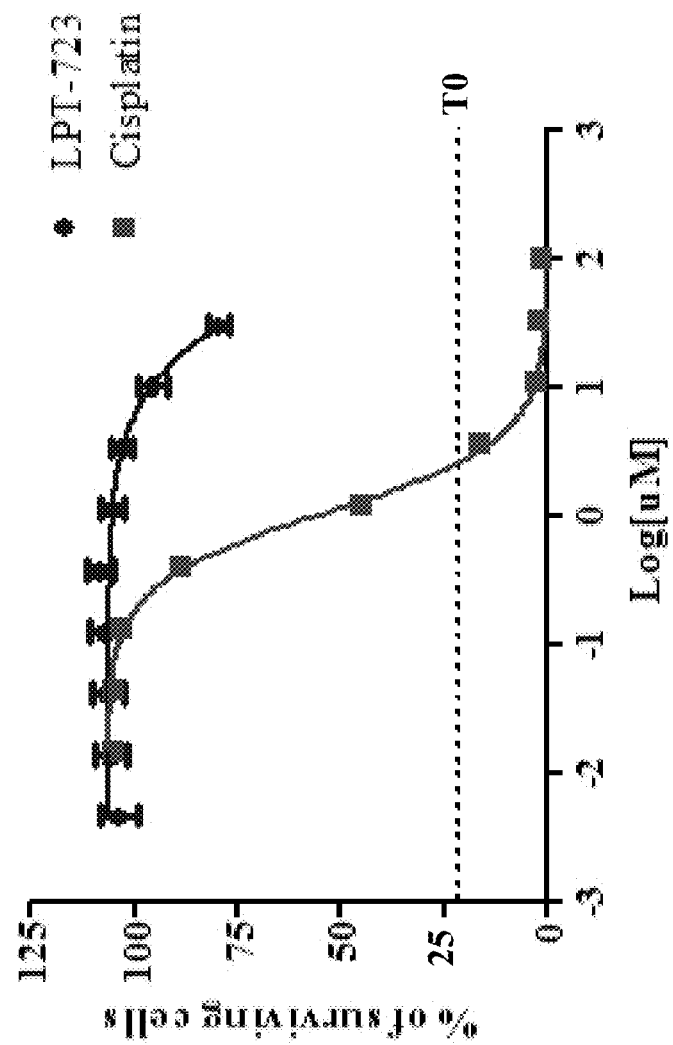

FIG. 17A-FIG. 17B show LPT-723 monotherapy and combination therapy in an A20 lymphoma cancer syngeneic model. FIG. 17A shows median tumor volume for Groups 1-4 at the same dosing schedule as mice in FIG. 16. There were no significant changes in body weights. N=10 animals per group. FIG. 17B shows an in vitro cell viability assay showing that LPT-723 does not directly kill A20 cells ($IC_{50}$=84.1 μM).

Figure 18A:
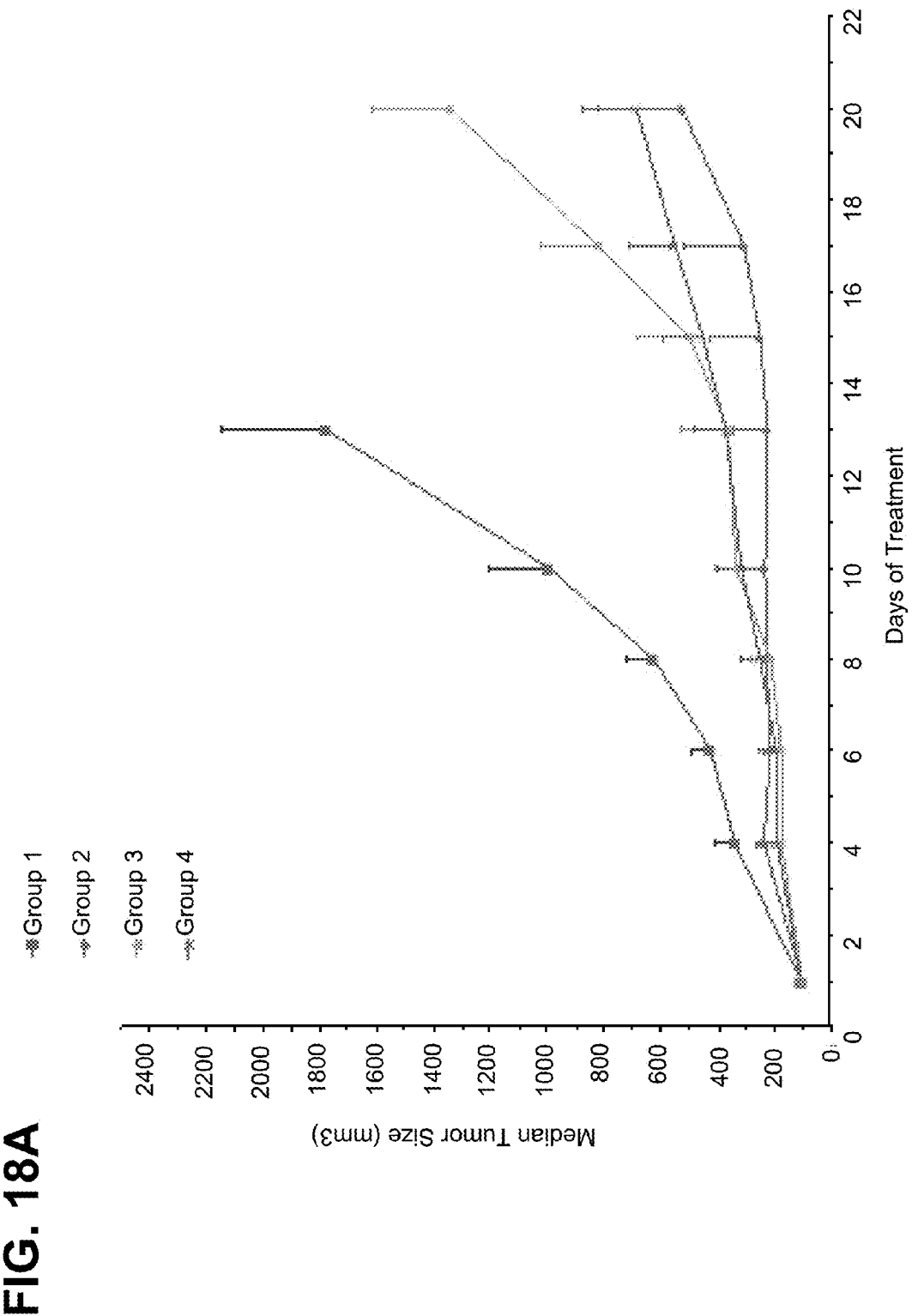
Figure 18B:
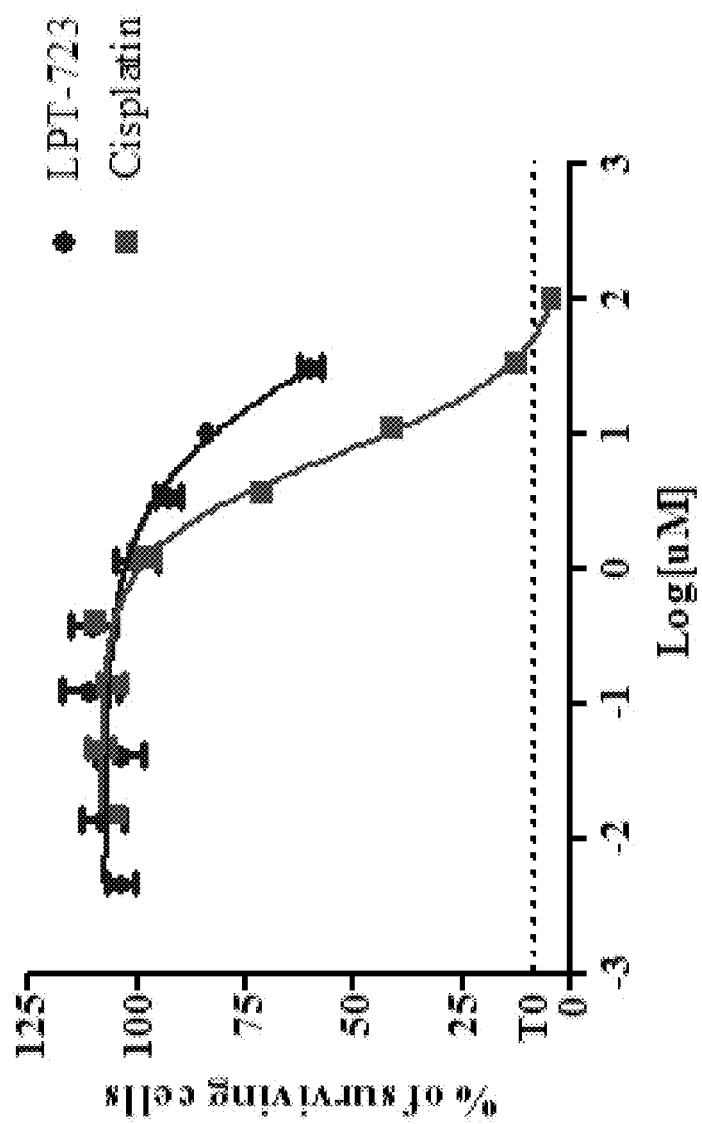

FIG. 18A-FIG. 18B show LPT-723 monotherapy and combination therapy in an MBT-2 bladder cancer syngeneic model. FIG. 18A shows median tumor volume for Groups 1-4 at the same dosing schedule as mice in FIG. 16A. There were no significant changes in body weights. N=10 animals per group. FIG. 18B shows an in vitro cell viability assay showing that LPT-723 does not directly kill MBT-2 cells ($IC_{50}$=45.49 μM).

Figure 19A:
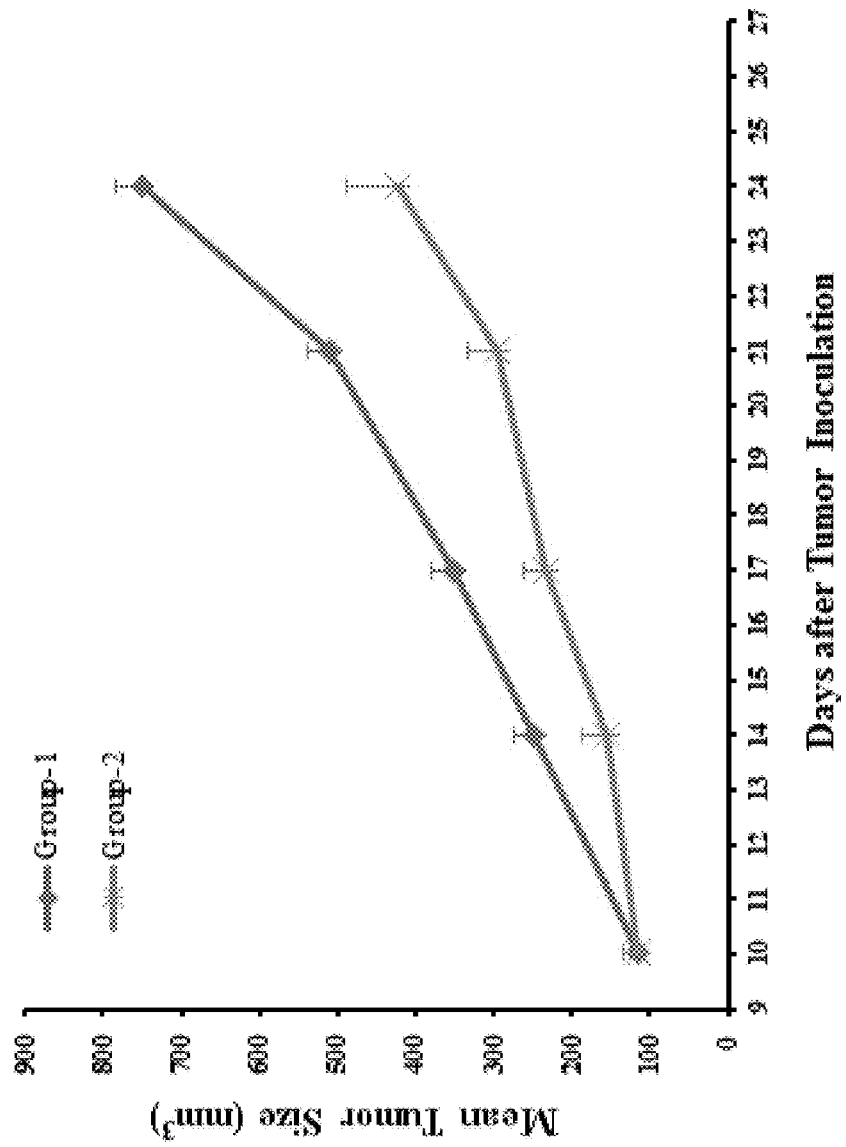
Figure 19B:
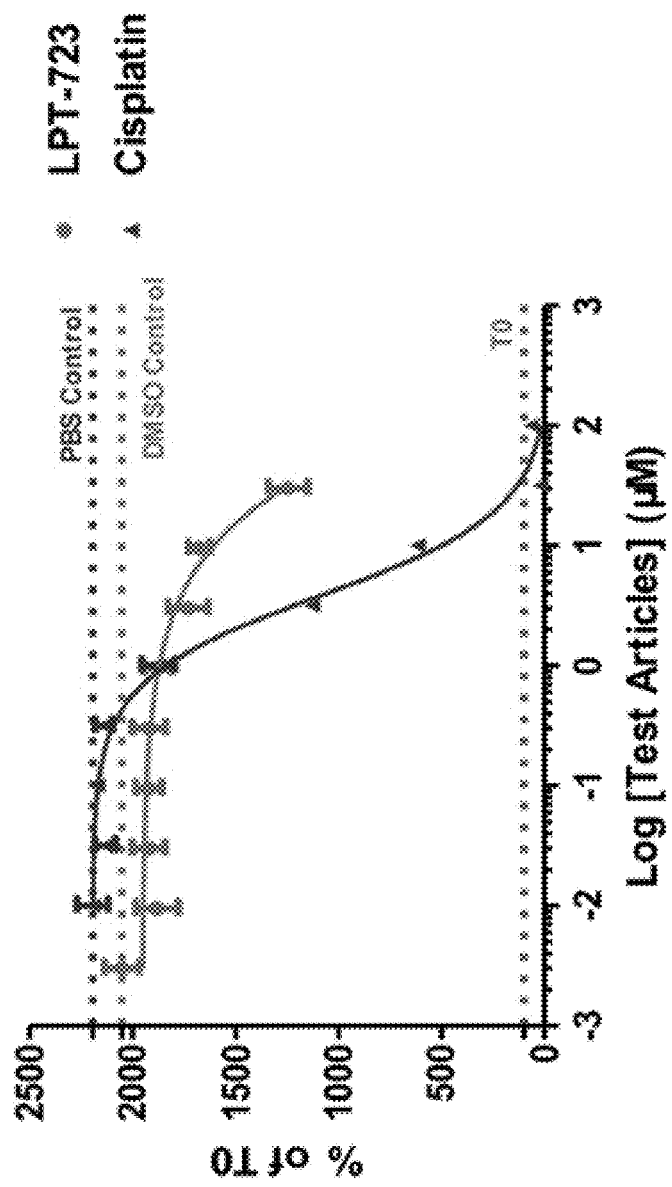

FIG. 19A-FIG. 19B show LPT-723 monotherapy in a HCT116 colon xenograft model tested with vehicle and LPT-723 (30 mg/kg) only. LPT-723 monotherapy activity demonstrated 45% tumor growth inhibition (FIG. 19A) despite no activity of LPT-723 up to 30 μM in vitro on HCT116 cells in culture (FIG. 19B). Tumor growth inhibition results suggest that LPT-723 modulates the tumor stromal microenvironment rather than acting through a direct tumor cell effect.

DETAILED DESCRIPTION OF THE INVENTION

One embodiment of the present invention is a method for treating or ameliorating the effects of a disorder in a subject comprising administering to the subject an effective amount of a first agent, which is a compound of formula (I):

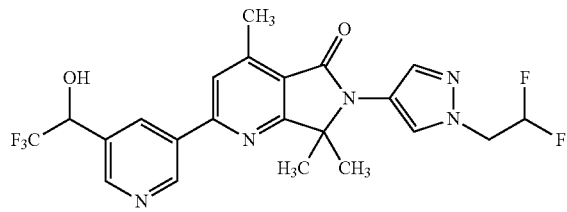 [SMILES: Cc1cc(-c2cncc(C(O)C(F)(F)F)c2)nc2c1C(=O)N(c1cnn(CC(F)F)c1)C2(C)C]

or a pharmaceutically acceptable salt thereof and a second agent, which is an immune checkpoint inhibitor.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

The terms "administering", "administration" and variants thereof (particularly "administering" a compound) as used herein in reference to the combinations of the present invention means introducing the components into the body of a subject, such as a human, in need of such treatment.

In some aspects of this and other embodiments the first and second agents are administered as a single unit dose. In other aspects, the first and second agents are co-administered. In yet other aspects the first agent is administered prior to the second agent. In yet other aspects the second agent is administered prior to the first agent.

In some aspects of this and other embodiments, the administration of the first and second agents to the subject provides a synergistic effect in the treatment of the disorder.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

In some aspects of this and other embodiments, the subject is a mammal. Preferably, the mammal is selected from the group consisting of humans, primates, farm animals, and domestic animals. More preferably, the mammal is a human.

In the present invention, an "effective amount" or a "therapeutically effective amount" of an agent, monoclonal antibody, or fragment thereof or a compound or composition disclosed herein is an amount of such material that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of any active agent disclosed herein or a composition containing the same will be that amount of the active agent or composition, which is the lowest dose effective to produce the desired effect.

A suitable, non-limiting example of a dosage of a compound of the present invention, and a monoclonal antibody, or an antigen binding fragment disclosed herein is from about 1 mg/kg to about 2400 mg/kg per day, such as from about 1 mg/kg to about 1200 mg/kg per day, including from about 50 mg/kg to about 1200 mg/kg per day. Other representative dosages of such agents include about 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of the compounds, antibodies, and antibody fragments disclosed herein may be administered as two, three, four, five, six or more sub-doses, administered separately at appropriate intervals throughout the day.

As used herein, a "pharmaceutically acceptable salt" means a salt of the compounds of the present invention which are pharmaceutically acceptable, as defined herein, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The term "immune checkpoint inhibitor", as used herein, refers to a substance that blocks the activity of molecules involved in attenuating the immune response. Examples of immune checkpoint inhibitors include, but are not limited to inhibitors of CTLA-4, PD-1, LAG-3, B7-H3, B7-H4, TIM3, A2AR, and IDO.

In some aspects of this and other embodiments the immune checkpoint inhibitor is selected from a group consisting of an anti-PD-1 antibody, an anti PD-L1 antibody, an anti-CTLA-4 antibody, and combinations thereof. Preferably, the immune checkpoint inhibitor is selected from a group consisting of nivolumab (Bristol-Myers Squibb), pembrolizumab (Merck), pidilizumab (Curetech), AMP-224 (GlaxoSmithKline/Amplimmune), MPDL3280A (Roche), MDX-1105 (Medarex, Inc./Bristol Myer Squibb), MEDI-4736 (Medimmune/AstraZeneca), arelumab (Merck Serono), ipilimumab (YERVOY, (Bristol-Myers Squibb), tremelimumab (Pfizer), pidilizumab (CureTech, Ltd.), IMP321 (Immutep S.A.), MGA271 (Macrogenics), BMS-986016 (Bristol-Meyers Squibb), lirilumab (Bristol-Myers Squibb), urelumab (Bristol-Meyers Squibb), PF-05082566 (Pfizer), IPH2101 (Innate Pharma/Bristol-Myers Squibb), MEDI-6469 (MedImmune/AZ), CP-870,893 (Genentech), Mogamulizumab (Kyowa Hakko Kirin), Varlilumab (CeliDex Therapeutics), Avelumab (EMD Serono), Galiximab (Biogen Idec), AMP-514 (Amplimmune/AZ), AUNP 12 (Aurigene and Pierre Fabre), Indoximod (NewLink Genetics), NLG-919 (NewLink Genetics), INCB024360 (Incyte) and combinations thereof.

As used herein, an "antibody" and "antigen-binding fragments thereof" encompass naturally occurring immunoglobulins (e.g., IgM, IgG, IgD, IgA, IgE, etc.) as well as non-naturally occurring immunoglobulins, including, for example, single chain antibodies, chimeric antibodies (e.g., humanized murine antibodies), heteroconjugate antibodies (e.g., bispecific antibodies), Fab', F(ab')$_2$, Fab, Fv, and rIgG. See, e.g., Pierce Catalog and Handbook, 1994-1995 (Pierce Chemical Co., Rockford, Ill.); Kuby et al., 1998. As used herein, an "antigen-binding fragment" is a portion of the full length antibody that retains the ability to specifically recognize the antigen, as well as various combinations of such portions.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

Full length antibodies can be proteolytically digested down to several discrete, functional antibody fragments, which retain the ability to recognize the antigen. For example, the enzyme papain can be used to cleave a full length immunoglobulin into two Fab fragments and an Fc fragment. Thus, the Fab fragment is typically composed of two variable domains and two constant domains from the heavy and light chains. The Fv region is usually recognized as a component of the Fab region and typically comprises two variable domains, one from each of the heavy ($V_H$, "heavy chain variable region", as used herein) and light ($V_L$ "light chain variable region", as used herein) chains. The enzyme pepsin cleaves below the hinge region, so a F(ab')$_2$ fragment and a pFc' fragment is formed. F(ab')$_2$ fragments are intact antibodies that have been digested, removing the constant (Fc) region. Two Fab' fragments can then result from further digestion of F(ab')$_2$ fragments. Examples of antigen-binding fragments include, but are not limited to, Fv, Fab, Fab', Fab'-SH, F(ab')$_2$, diabodies, tribodies, scFvs, and single-domain antibodies (dAbs).

Typically, a full length antibody has at least one heavy and at least one light chain. Each heavy chain contains a variable domain ($V_H$) and typically three or more constant domains ($C_H1$, $C_H2$, $C_H3$, etc.), while each light chain contains a variable domain ($V_L$) and a constant domain $C_L$. Light and heavy chain variable regions contain four "framework" regions interrupted by three hypervariable regions, also called "complementarity-determining regions" or "CDRs". The extent of the framework regions and CDRs have been defined. See, e.g., Kabat et al., U.S. Dept. of Health and Human Services, Sequences of Proteins of Immunological Interest (1983) and Chothia et al., J. Mol. Biol. 196:901-917 (1987). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody, whereas a $V_L$ CDR1 is the CDR1 from the variable domain of the light chain of the antibody.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made, e.g., by the hybridoma method first described by Kohler et al., Nature 256: 495 (1975), and as modified by the somatic hybridization method as set forth above; or may be made by other recombinant DNA methods (see, e.g., U.S. Pat. No. 4,816,567).

Additional types of antibodies that may be part of the monoclonal antibodies of the present invention include, but are not limited to, chimeric, humanized, and human antibodies. For application in man, it is often desirable to reduce immunogenicity of antibodies originally derived from other species, like mouse. This can be done by construction of chimeric antibodies, or by a process called "humanization". In this context, a "chimeric antibody" is understood to be an antibody comprising a domain (e.g. a variable domain) derived from one species (e.g. mouse) fused to a domain (e.g. the constant domains) derived from a different species (e.g. human).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol 2:593-596 (1992)). Humanization can be essentially performed, e.g., following the method of Winter and co-workers (Jones et al., Nature 321:522-525 (1986); Riechmann et al., Nature 332:323-3'27 (1988); Verhoeyen et al., Science 239:1534-1536 (1988)), by substituting rodent CDRs or CDR sequences for the corresponding sequences of a human antibody.

Furthermore, technologies have been developed for creating antibodies based on sequences derived from the human genome, for example by phage display or using transgenic animals (see, e.g., WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2)189-203; Lonberg N, Huszar D. "Human antibodies from transgenic mice". Int Rev Immunol. 1995; 13(1): 65-93.; Bruggemann M, Taussig M J. "Production of human antibody repertoires in transgenic mice". Curr Opin Biotechnol. 1997 August; 8(4):455-8.). Such antibodies are "human antibodies" in the context of the present invention.

As used herein, a "recombinant" antibody is any antibody whose production involves expression of a non-native DNA sequence encoding the desired antibody structure in an organism. In the present invention, recombinant antibodies include tandem scFv (taFv or $scFv_2$), diabody, $dAb_2/VHH_2$, knob-into-holes derivatives, SEED-IgG, heteroFc-scFv, Fab-scFv, scFv-Jun/Fos, Fab'-Jun/Fos, tribody, $DNL-F(ab)_3$, $scFv_3$-CH1/CL, Fab-$scFv_2$, IgG-scFab, IgG-scFv, scFv-IgG, $scFv_2$-Fc, $F(ab')_2$-$scFv_2$, scDB-Fc, scDb-CH3, Db-Fc, $scFv_2$-H/L, DVD-Ig, tandAb, scFv-dhlx-scFv, $dAb_2IgG$, $dAb$-IgG, dAb-Fc-dAb, and combinations thereof.

Variable regions of antibodies are typically isolated as single-chain Fv (scFv) or Fab fragments. ScFv fragments are composed of $V_H$ and $V_L$ domains linked by a short 10-25 amino acid linker. Once isolated, scFv fragments can be genetically linked with a flexible peptide linker such as, for example, one or more repeats of Ala-Ala-Ala, Gly-Gly-Gly-Gly-Ser, etc. The resultant peptide, a tandem scFv (taFv or $scFv_2$) can be arranged in various ways, with $V_H$-$V_L$ or $V_L$—$V_H$ ordering for each scFv of the taFv. (Kontermann, R. E. In: Bispecific Antibodies. Kontermann R E (ed.), Springer Heidelberg Dordrecht London New York, pp. 1-28 (2011)).

As used herein, the term "epitope" refers to the portion of the antigen which is recognized by the antibody or antigen binding fragment. A single antigen (such as an antigenic polypeptide) may have more than one epitope. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes formed from contiguous amino acids are typically retained on exposure to denaturing solvents, whereas epitopes formed by tertiary folding are typically lost on treatment with denaturing solvents.

In some aspects of this and other embodiments, the compound of formula (I) is selected from the group consisting of a substantially pure R-enantiomer thereof, a substantially pure S-enantiomer thereof, and a racemic mixture of the R- and S-enantiomers.

Preferably, the compound of formula (I) is a substantially pure R-enantiomer:

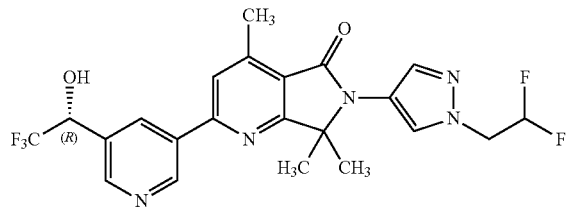

or a pharmaceutically acceptable salt thereof.

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers, optical isomers, and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts as disclosed in more detail herein or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The stereoisomers may also be separated by usual techniques known to those skilled in the art including fractional crystallization of the bases or their salts or chromatographic techniques such as LC or flash chromatography. The (+) enantiomer can be separated from the (−) enantiomer using techniques and procedures well known in the art, such as that described by J. Jacques, et al., antiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

The compound of formula (I) is referred to interchangeably as "LPT-723". It is understood that the present invention also includes other enantiomeric forms and racemic mixtures of LPT-723. The R isomer is a preferred agent.

In some aspects of this and other embodiments, the disorder is cancer, Preferably, the cancer is selected from the group consisting of bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, multiple myeloma, neuroblastoma, neuroendocrine cancer, ovarian cancer, pancreatic cancer, prostate cancer, rectal cancer, renal cell carcinoma, rhabdoid cancer, sarcomas, and urinary track cancer. More preferably, the cancer is selected from the group consisting of bladder cancer, colon cancer, lung cancer, lymphoma, and pancreatic cancer.

Another embodiment of the present invention is a method for treating or ameliorating the effects of a cancer in a subject comprising administering to the subject an effective amount of a compound of formula (I):

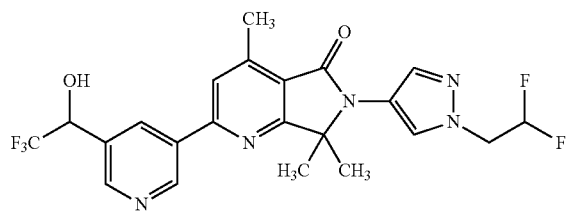 [SMILES: Cc1cc(-c2cncc(C(O)C(F)(F)F)c2)nc2c1C(=O)N(c1cnn(CC(F)F)c1)C2(C)C]

or a pharmaceutically acceptable salt thereof.

In some aspects of this and other embodiments, the cancer is selected from the group consisting of bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, multiple myeloma, neuroblastoma, neuroendocrine cancer, ovarian cancer, pancreatic cancer, prostate cancer, rectal cancer, renal cell carcinoma, rhabdoid cancer, sarcomas, and urinary track cancer. Preferably, the cancer is colon cancer.

Another embodiment of the present invention is a method for modulating a stromal microenvironment of a cancer comprising contacting the stromal microenvironment of the cancer with a compound of formula (I):

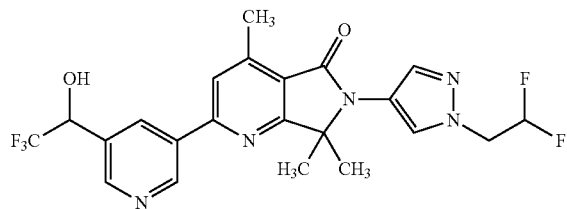 [SMILES: Cc1cc(-c2cncc(C(O)C(F)(F)F)c2)nc2c1C(=O)N(c1cnn(CC(F)F)c1)C2(C)C]

or a pharmaceutically acceptable salt.

As used herein, "tumors" and "cancers" are used interchangeably. Tumors may be benign or malignant. As used herein, the "stromal microenvironment" includes those stromal cells that are in a tumor cell's microenvironment and support the growth of tumor cells.

In this embodiment, "contacting" means bringing, e.g., LPT-723, the immune checkpoint inhibitor, and/or one or more additional therapeutic agents into close proximity to the stromal microenvironment. This may be accomplished using conventional techniques of drug delivery to mammals or in the in vitro situation by, e.g., providing the LPT-723, the immune checkpoint inhibitor, and/or one or more additional therapeutic agents to a culture media in which the cancer cells are located.

Another embodiment of the present invention is a composition for treating or ameliorating the effects of a disorder in a subject, the composition comprising a first agent, which is a compound of formula (I):

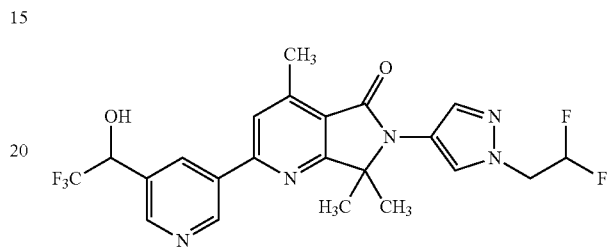

or a pharmaceutically acceptable salt thereof and a second agent, which is an immune checkpoint inhibitor.

In some aspects of this and other embodiments, the composition is a pharmaceutical composition further comprising a pharmaceutically acceptable carrier or diluent. In the present invention, all of the compounds may be combined with pharmaceutically acceptable carriers or diluents.

The compositions and pharmaceutical compositions of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the compositions and pharmaceutical compositions of the present invention may be administered in conjunction with other treatments. Each composition and pharmaceutical composition of the present invention may be encapsulated or otherwise protected against gastric or other secretions, if desired.

The compositions and pharmaceutical compositions of the invention may comprise one or more active ingredients in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The compositions and pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions and pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. Any active ingredient of the invention can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions and pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. Compositions and pharmaceutical compositions of the present invention which are suitable for vaginal administration also include pessaries, tampons, creams, gels, pastes, foams or spray formulations containing such pharmaceutically-acceptable carriers as are known in the art to be appropriate.

Dosage forms for topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

Compositions and pharmaceutical compositions of the present invention suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., a composition or a pharmaceutical composition of the present invention), it is desirable to slow its absorption from subcutaneous or intramuscular injection. This may be accomplished by the use of a liquid suspension of crystalline or amorphous material having poor water solubility.

The rate of absorption of the active any active agent/composition of the invention then depends upon its rate of dissolution which, in turn, may depend upon crystal size and crystalline form. Alternatively, delayed absorption of a parenterally-administered any active agent/composition of the invention may be accomplished by dissolving or suspending the active agent/composition in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

Any formulation of the invention may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

In some aspects of this and other embodiments, the first and second agents in the composition are in separate unit dose forms. In other aspects, the first and second agents are in a single unit dose form.

Another embodiment of the present invention is a kit comprising a first agent, which is a compound of formula (I):

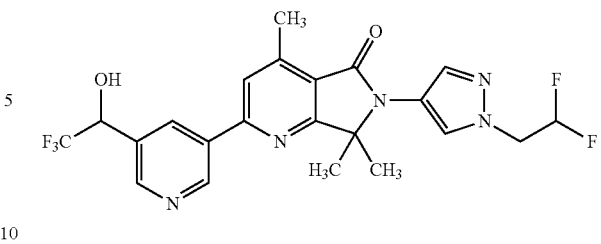

or a pharmaceutically acceptable salt thereof and a second agent, which is an immune checkpoint inhibitor, together with instructions for their use.

The kits may also include suitable storage containers, e.g., ampules, vials, tubes, etc., for each agent of the present invention (which may e.g., may be in the form of pharmaceutical compositions) and other reagents, e.g., buffers, balanced salt solutions, etc., for use in administering the agents to subjects. The agents of the invention and other reagents may be present in the kits in any convenient form, such as, e.g., in a solution or in a powder form. The kits may further include a packaging container, optionally having one or more partitions for housing the pharmaceutical composition and other optional reagents.

Additional Definitions

As used herein, terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "amino acid" means naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. An "amino acid analog" means compounds that have the same basic chemical structure as a naturally occurring amino acid, e.g., a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. An "amino acid mimetic" means a chemical compound that has a structure that is different from the general chemical structure of an amino acid, but that functions similarly to a naturally occurring amino acid.

"Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (siRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

The nucleic acid may also be an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; 0- and N-alkylated nucleotides, e.g. N6-methyl adenosine are suitable. The 2'-OH-group may be replaced by a group selected from H, OR, R, halo, SH, SR, NH$_2$, NHR, NR$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No. 20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6, 9, and 7.0 are explicitly contemplated.

The following examples are provided to further illustrate the methods of the present invention. These examples are illustrative only and are not intended to limit the scope of the invention in any way.

EXAMPLES

The following examples are provided to further illustrate certain aspects of the present invention. These examples are illustrative only and are not intended to limit the scope of the invention in any way.

Example 1

Prophylactic Colon26 Colon Cancer Model:

Charles River (CR) BALB/c mice were implanted with Colon26 murine colon cancer cells on Day 1, and treatment was initiated on Day 3 with control (vehicle), anti-CTLA-4 (clone 4F10), anti-PD-1 (clone RMP1-14), anti-CTLA-4/anti-PD-1 combination, LPT-723 (10 mpk, 30 mpk), anti-CTLA-4/LPT-723 (10 mpk, 30 mpk) combination, or anti-PD-1/LPT-723 (10 mpk, 30 mpk) combination. Anti-CTLA-4 was dosed i.p. on Day 8 at a dose of 100 µg/animal and on Days 11, and 14 at a dose of 50 µg/animal. Anti-PD-1 was dosed i.p. twice a week for two weeks starting on Day 3 at a dose of 100 µg/animal. LPT-723 was dosed per os (p.o.) twice a day starting on Day 3. Table 1 shows the response summary for groups 1-4:

TABLE 1

Colon26-e255 EDC Response Summary

| Group | n | Treatment Regimen 1 | | | Treatment Regimen 2 | | | Median TTE | % T-C | TGD | MTV (n), Day 57 | TFS | NTRm | NTR |
|---|---|---|---|---|---|---|---|---|---|---|---|---|---|---|
| | | Agent | mg/kg | Schedule | Agent | mg/kg | Schedule | | | | | | | |
| 1# | 10 | Veh3 | — | bid to end (D3) | IgG | 100/ 50/50 | day Aug. 11, 2014 | 32 | — | — | 600 (1) | 0 | 0 | 0 |
| 2 | 10 | anti-CTLA4 | 100/ 50/50 | day Aug. 11, 2014 | | | | 29.6 | −2 | −7 | 0 (1) | 1 | 0 | 1 |
| 3 | 10 | anti-PD1 | 100* | biwk × 2 (D3) | — | — | — | 32.2 | 0 | 1 | 75 (1) | 0 | 0 | 4 |
| 4 | 5 | anti-PD1 | 100* | biwk × 2 (D3) | anti-CTLA4 | 100/ 50/50 | day Aug. 11, 2014 | 57 | 25 | 78 | 0 (5) | 4 | 0 | 0 |

Table 2 below shows the response summary for groups 1-3 and 11-16:

TABLE 2

Colon26-e255 EDC Response Summary

| Group | n | Treatment Regimen 1 | | | Treatment Regimen 2 | | | Median TTE | % TC | TGD | MTV (n), Day 57 | TFS | NTRm | NTR |
|---|---|---|---|---|---|---|---|---|---|---|---|---|---|---|
| | | Agent | mg/kg | Schedule | Agent | mg/kg | Schedule | | | | | | | |
| 1# | 10 | Veh3 | — | bid to end (D3) | IgG | 100/ 50/50 | day Aug. 11, 2014 | 32 | — | — | 600 (1) | 0 | 0 | 0 |
| 2 | 10 | anti-CTLA4 | 100/ 50/50 | day Aug. 11, 2014 | | | | 29.6 | −2 | −7 | 0 (1) | 1 | 0 | 1 |
| 3 | 10 | anti-PD1 | 100‡ | biwk × 2 (D3) | — | — | — | 32.2 | 0 | 1 | 75 (I) | 0 | 0 | 4 |
| 11 | 10 | MR237 | 10 | bid to end (D3) | — | — | — | 31.9 | −0 | 0 | — | 0 | 0 | |
| 12 | 10 | MR237 | 30 | bid to end (D3) | — | — | — | 33.7 | 1.7 | 5 | 0 (1) | 1 | 0 | 1 |
| 13 | 10 | MR237 | 10 | bid to end (D3) | anti-CTLA4 | 100/ 50/50 | day Aug. 11, 2014 | 57 | 25 | 78 | 0 (6) | 5 | 0 | 0 |
| 14 | 10 | MR237 | 30 | bid to end (D3) | anti-CTLA4 | 100/ 50/50 | day Aug. 11, 2014 | 57 | 25 | 78 | 0 (7) | 5 | 0 | 0 |
| 15 | 10 | MR237 | 10 | bid to end (D3) | anti-PDI | 100‡ | biwk × 2 (D3) | 52 | 20 | 63 | 0 (4) | 3 | 0 | 0 |
| 16 | 10 | MR237 | 30 | bid to end (D3) | anti-PD1 | 100‡ | biwk × 2 (D3) | 49.4 | 18 | 55 | 0 (4) | 4 | 0 | 0 |

Figure 1:
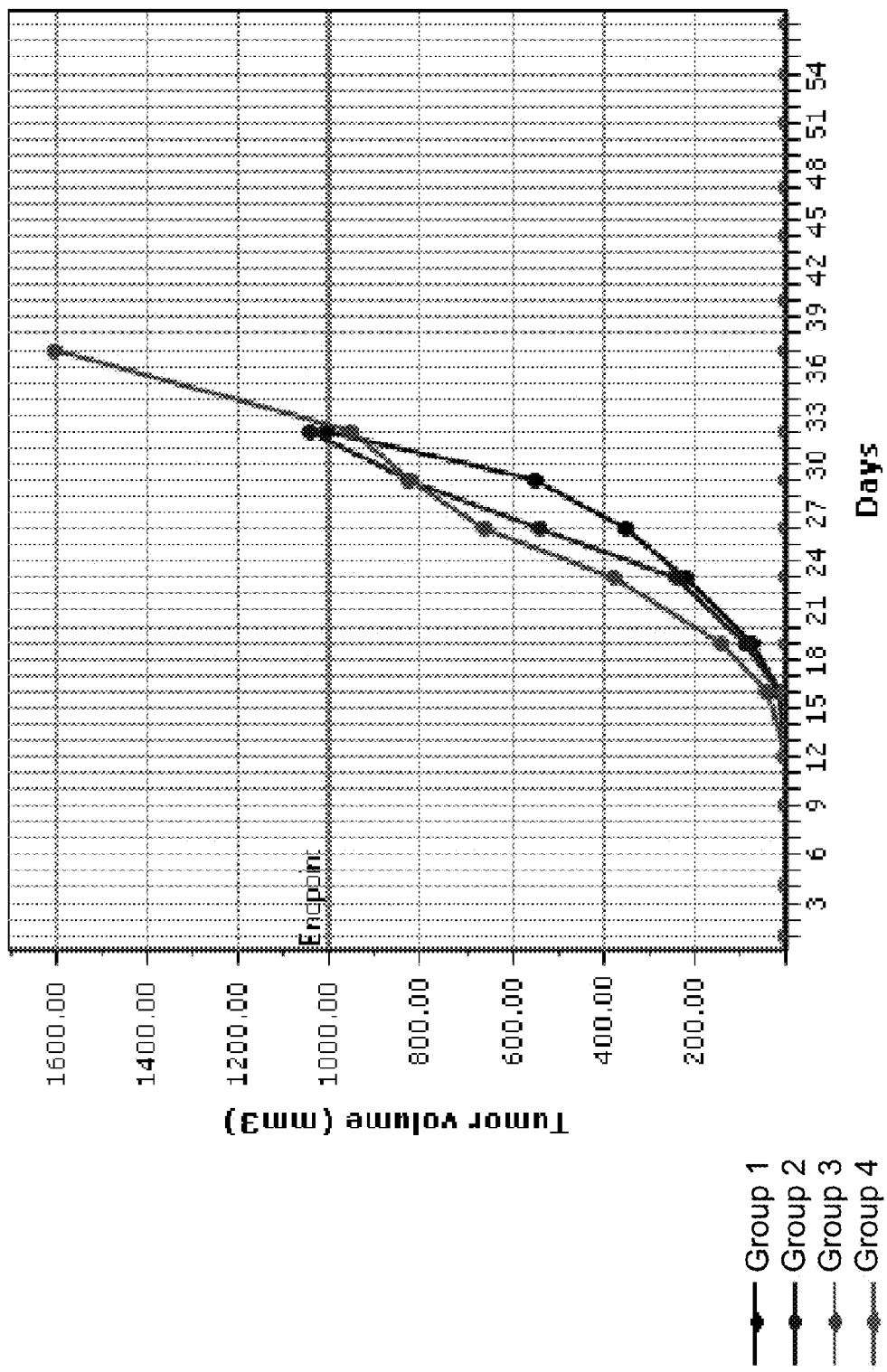
FIG. 1 shows a graph of median tumor volume for vehicle and checkpoint inhibitor control groups in a syngeneic mouse colon cancer model (Colon26) with an intact immune system. Data is displayed for 57 days of treatment. Group 1 mice (n=10) were given vehicle orally twice per day from day 3 to endpoint and hamster polyclonal IgG intraperitoneally (i.p.) (100 µg/animal day 8; 50 µg/animal days 11 and 14). Group 2 (n=10) received anti-CTLA-4 i.p. (100 µg/animal day 8; 50 µg/animal days 11 and 14). Group 3 (n=10) received anti-PD-1 i.p. (100 µg/animal biweekly starting day 3). Group 4 (n=5) received anti-PD-1 i.p. (100 µg/animal biweekly starting day 3) and anti-CTLA-4 i.p. (100 µg/animal day 8; 50 µg/animal days 11 and 14).
Figure 2:
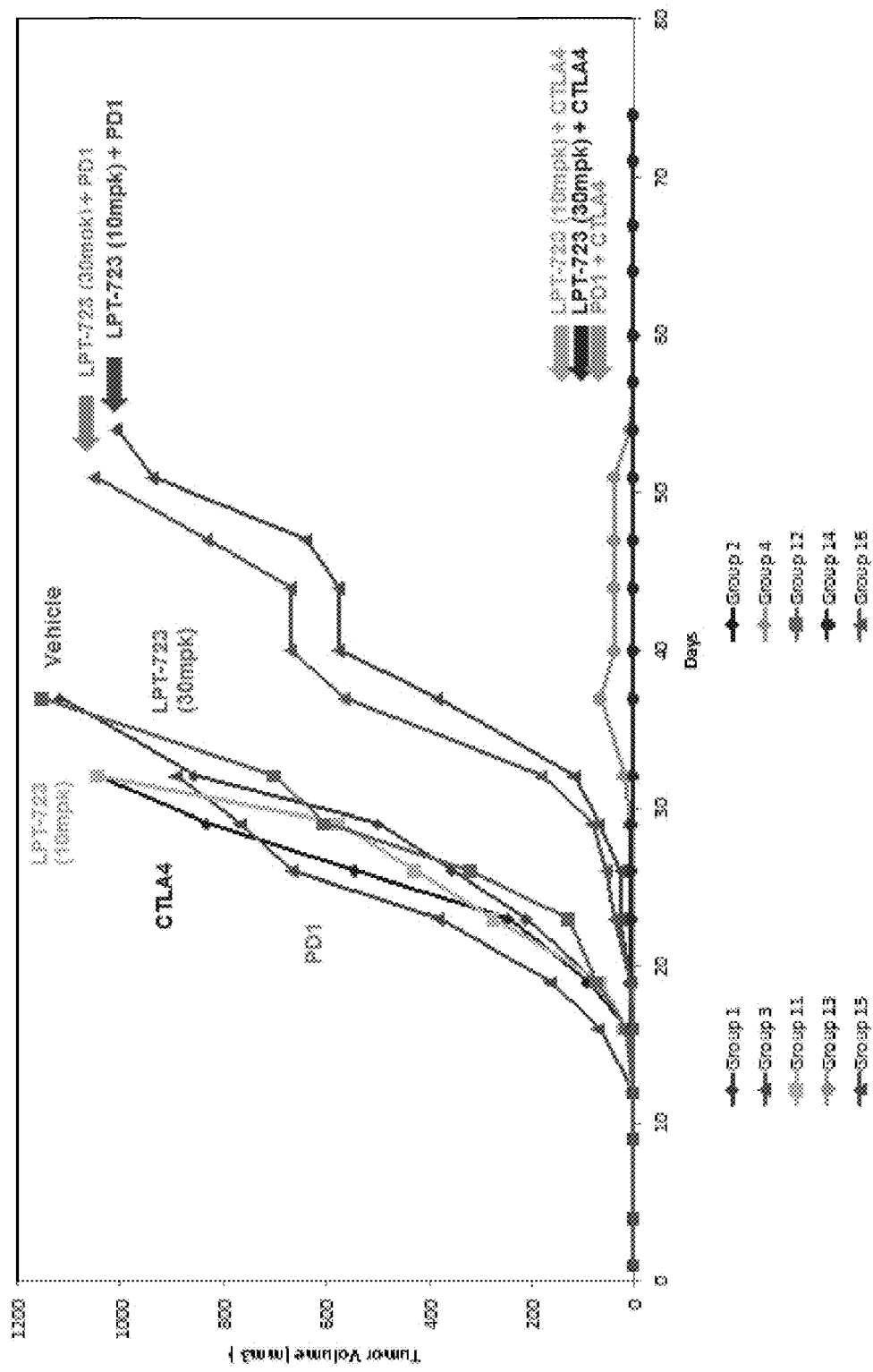
FIG. 2 shows a graph of mean tumor volume for up to 75 days of treatment in Colon26 mice. Groups 1-4 are control groups repeated from FIG. 1 for comparison. Group 11 mice were given LPT-723 (MR237) orally twice per day at 10 mg/kg from day 3 to endpoint. Group 12 mice were given LPT-723 orally twice per day at 30 mg/kg from day 3 to endpoint. Group 13 received LPT-723 orally twice per day at 10 mg/kg from day 3 to endpoint and anti-CTLA-4 i.p. (100 µg/animal day 8; 50 µg/animal days 11 and 14). Group 14 received LPT-723 orally twice per day at 30 mg/kg from day 3 to endpoint and anti-CTLA-4 i.p. (100 µg/animal day 8; 50 µg/animal days 11 and 14). Group 15 received LPT-723 orally twice per day at 10 mg/kg from day 3 to endpoint and anti-PD-1 i.p. (100 µg/animal biweekly starting day 3). Group 16 received LPT-723 orally twice per day at 30 mg/kg from day 3 to endpoint and anti-PD-1 i.p. (100 µg/animal biweekly starting day 3). N=10 for all groups.
Figure 3:
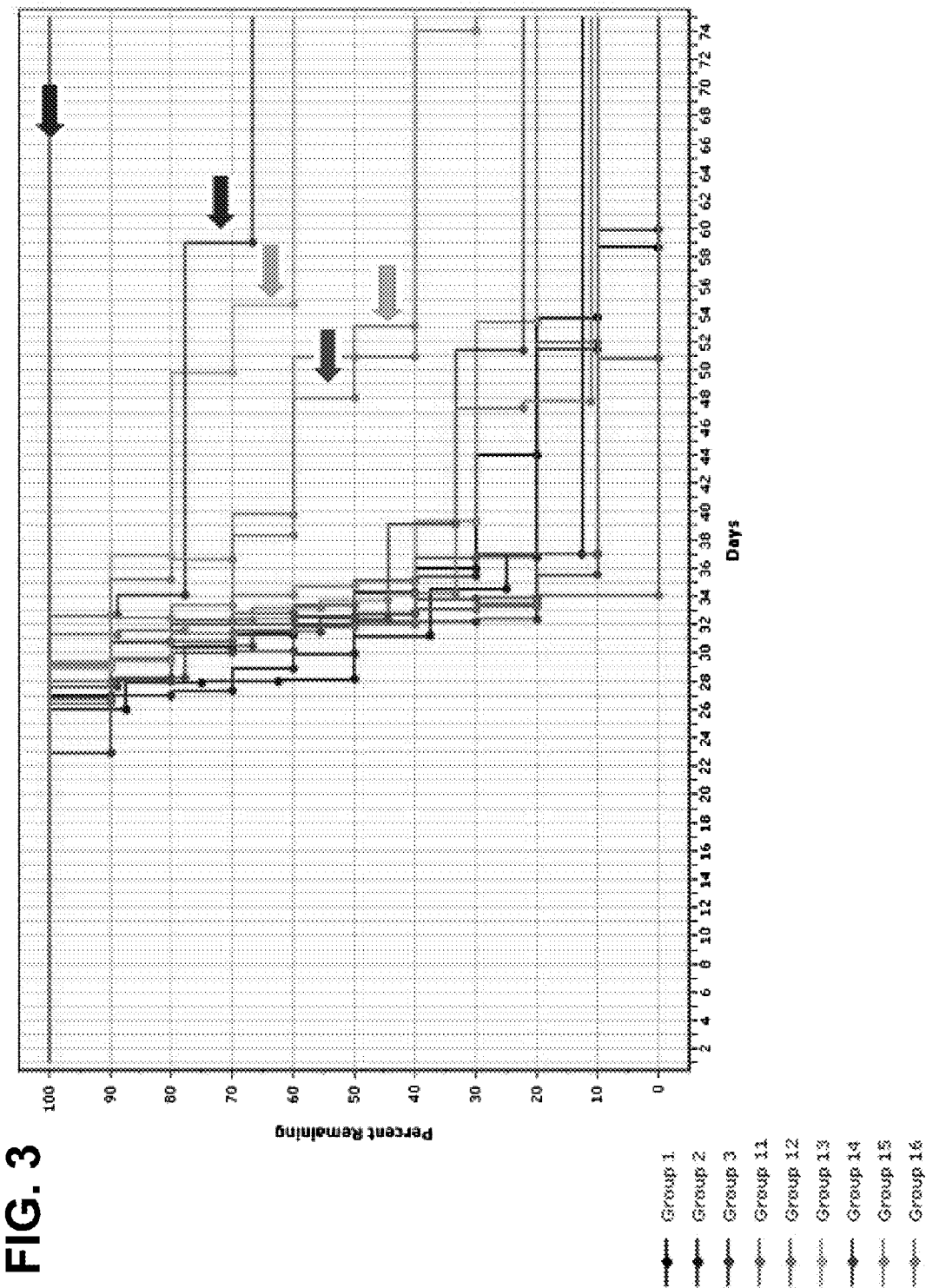
FIG. 3 shows a Kaplan-Meier survival plot of Groups 1-3 and 11-16 for 75 days of treatment. Groups 13-16 received LPT-723 and immune checkpoint inhibitor antibodies and are highlighted by arrows on the graph. The graph shows the percentage of animals surviving and provides evidence of synergy between LPT-723 and the checkpoint inhibitor antibodies that is not present in either treatment alone.
Figure 4:
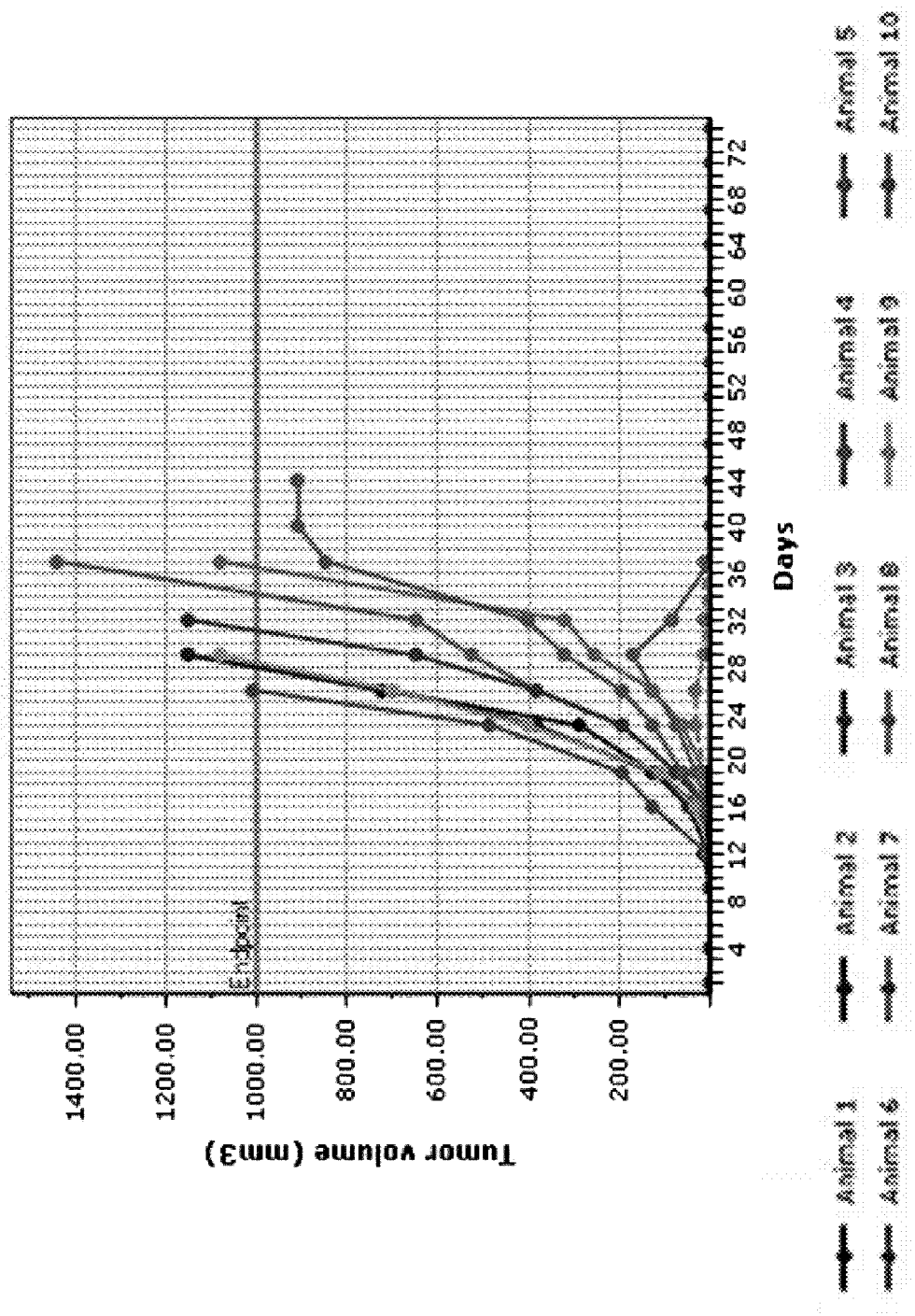
FIG. 4 is a graph showing tumor volume in individual animals from Group 2 during the course of the study. These animals received anti-CTLA-4 i.p. (100 µg/animal day 8; 50 µg/animal days 11 and 14).
Figure 5:
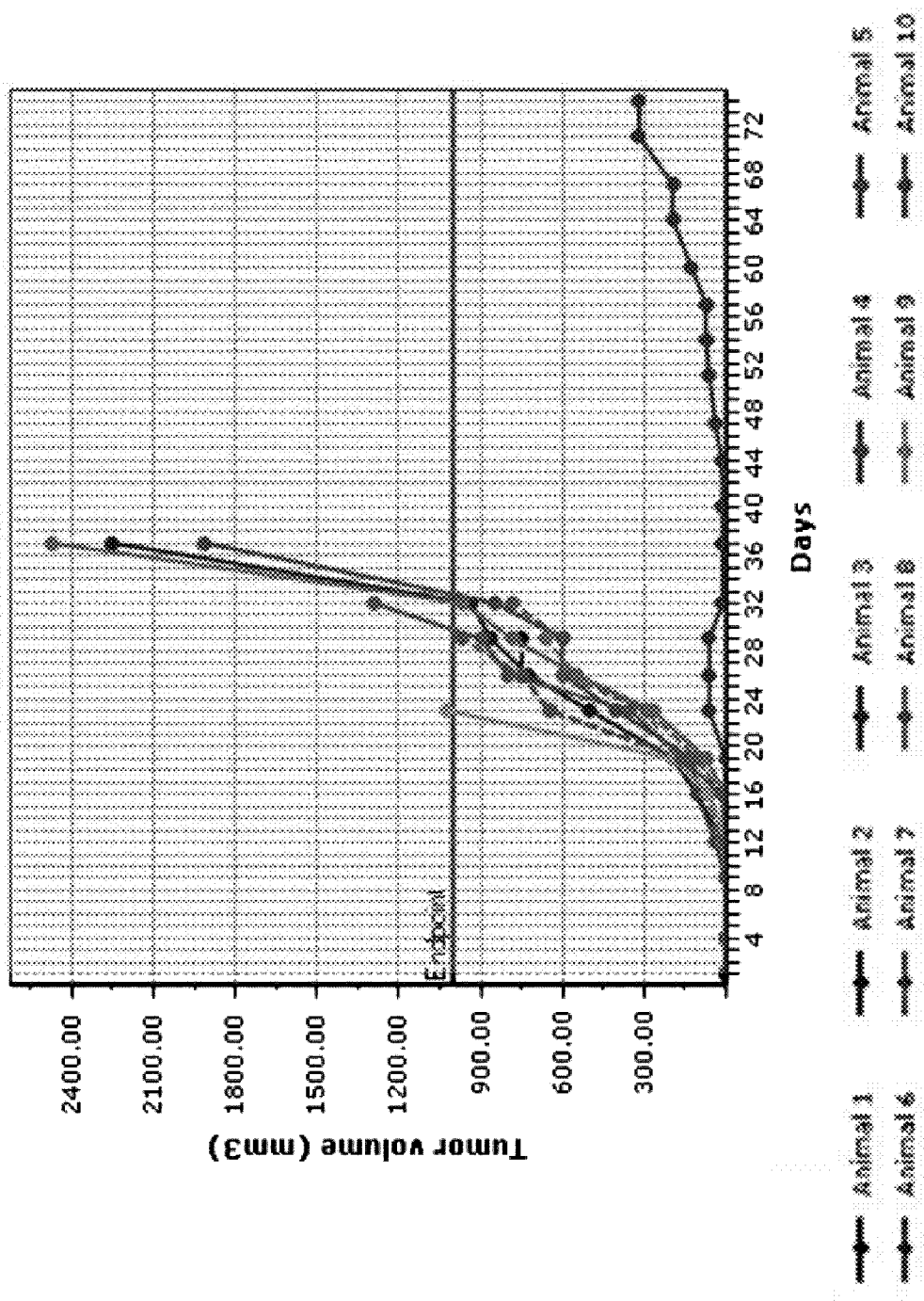
FIG. 5 is a graph showing tumor volume in individual animals from Group 3 during the course of the study. These animals received anti-PD-1 i.p. (100 µg/animal biweekly starting day 3).
Figure 6:
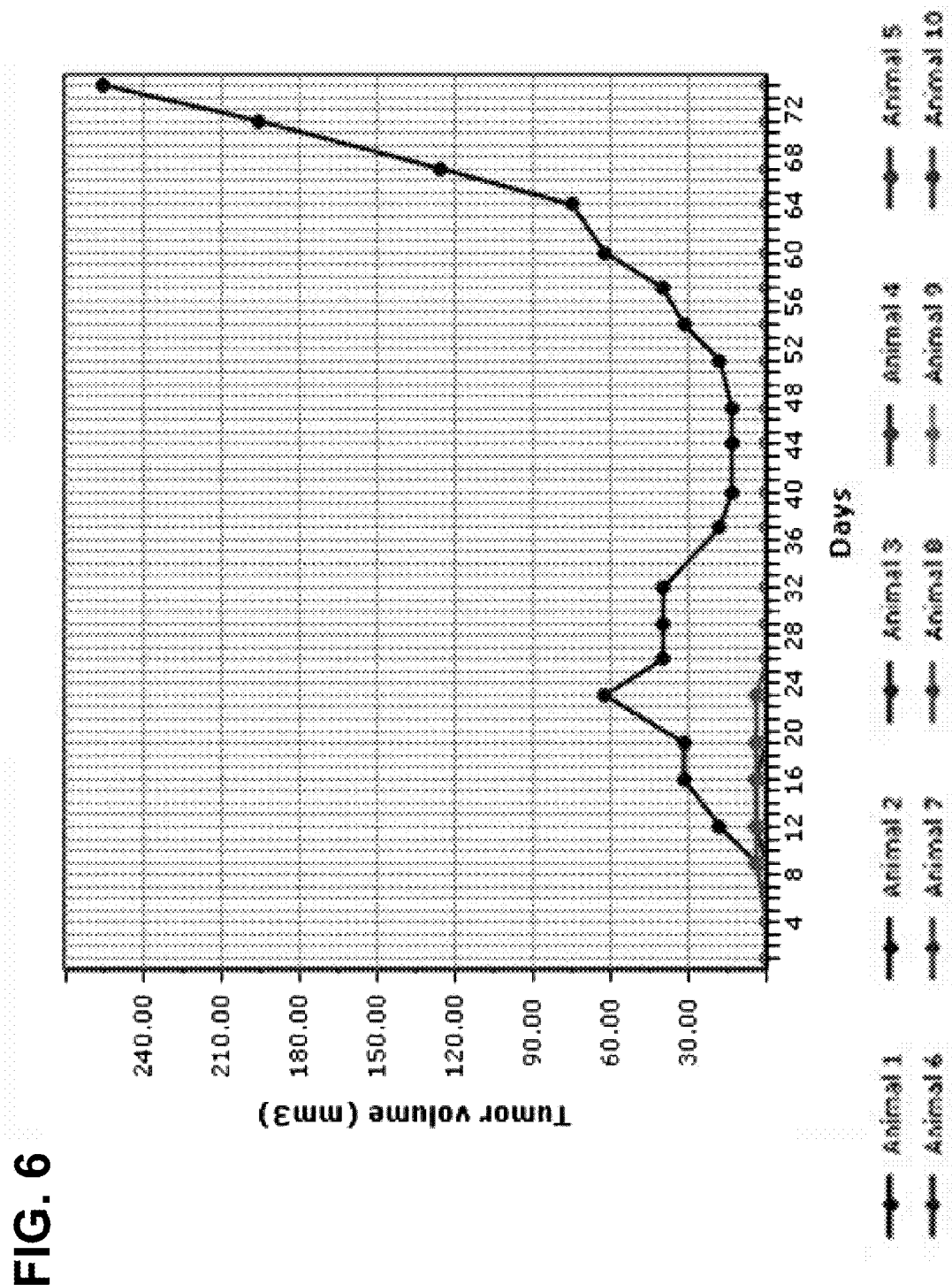
FIG. 6 is a graph showing tumor volume in individual animals from Group 4 during the course of the study. These animals received anti-CTLA-4 i.p. (100 µg/animal day 8; 50 µg/animal days 11 and 14) and anti-PD-1 i.p. (100 µg/animal biweekly starting day 3).
Figure 7:
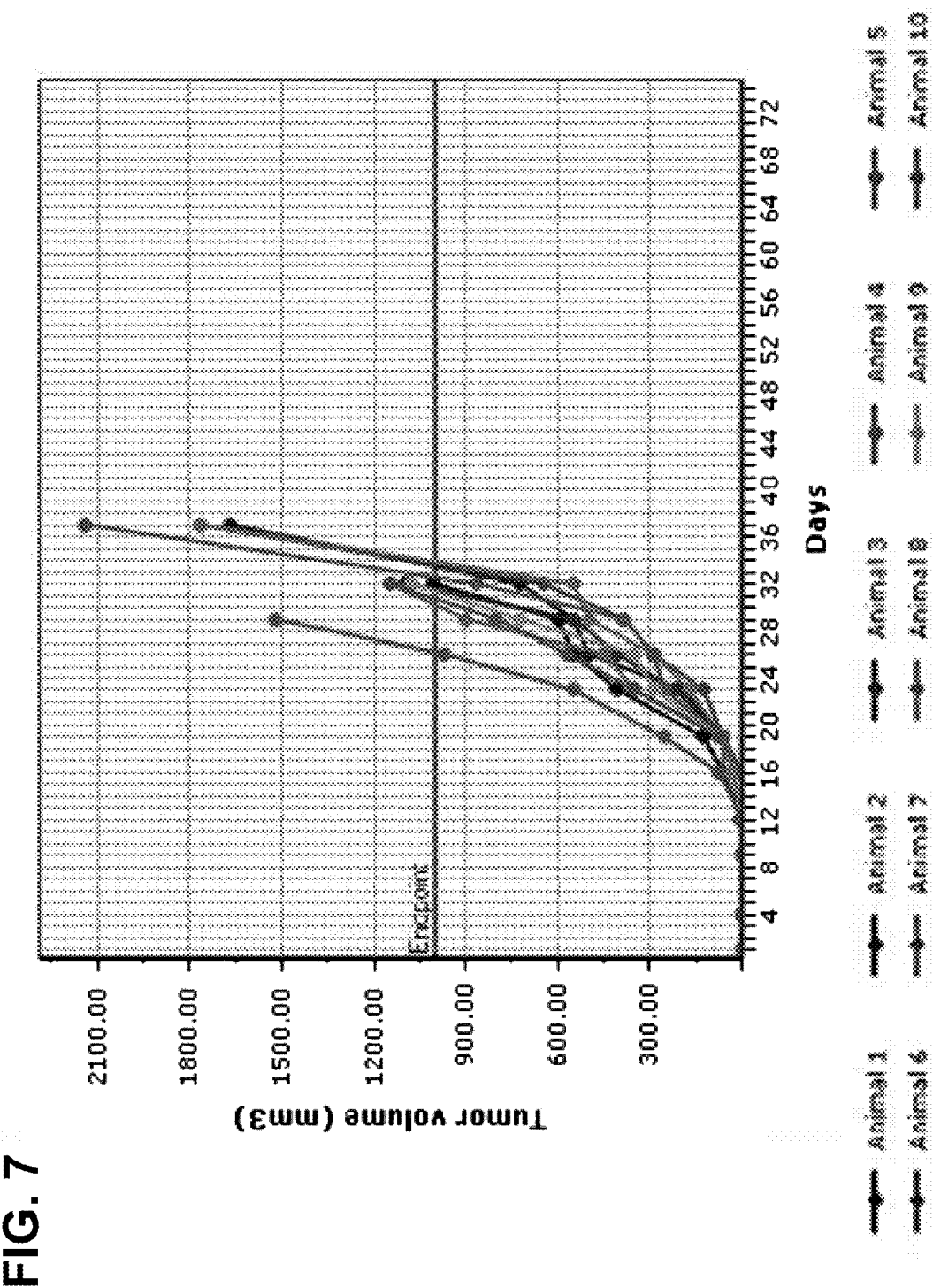
FIG. 7 is a graph showing tumor volume in individual animals from Group 11 during the course of the study. These animals received LPT-723 orally twice per day at 10 mg/kg from day 3 to endpoint.
Figure 8:
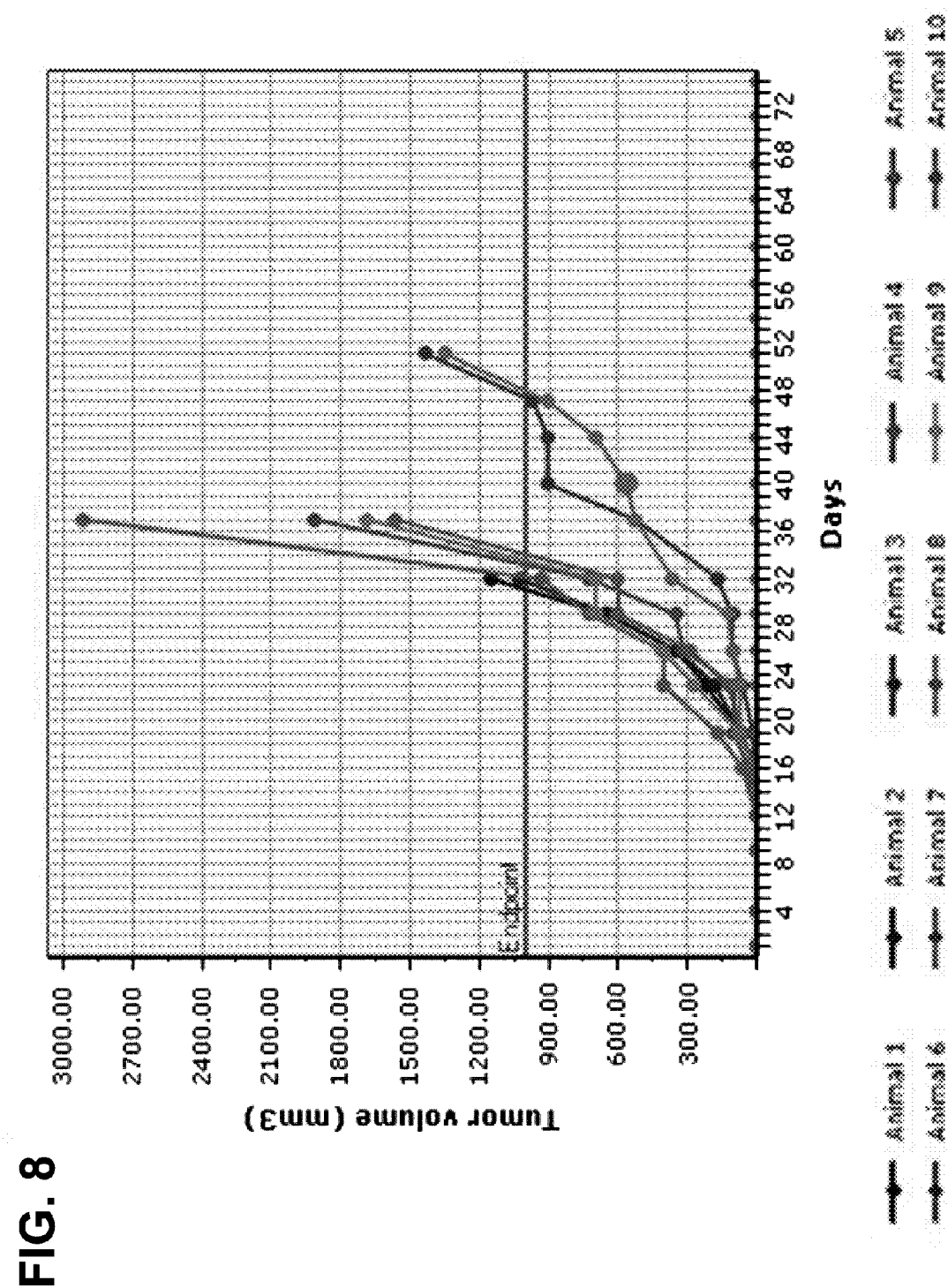
FIG. 8 is a graph showing tumor volume in individual animals from Group 12 during the course of the study. These animals received LPT-723 orally twice per day at 30 mg/kg from day 3 to endpoint.
Figure 9:
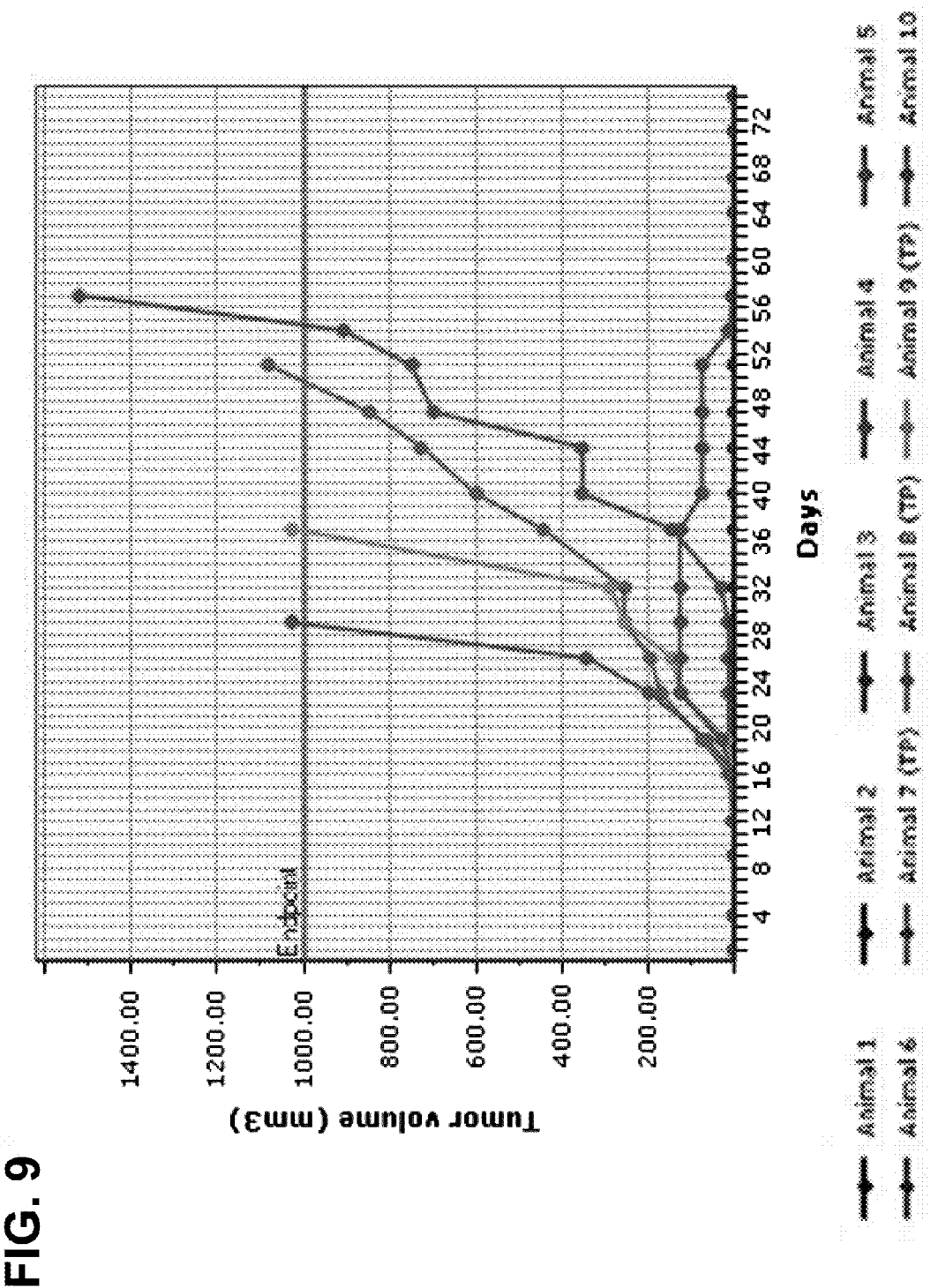
FIG. 9 is a graph showing tumor volume in individual animals from Group 13 during the course of the study. These animals received LPT-723 orally twice per day at 10 mg/kg from day 3 to endpoint and anti-CTLA-4 i.p. (100 µg/animal day 8; 50 µg/animal days 11 and 14).
Figure 10:
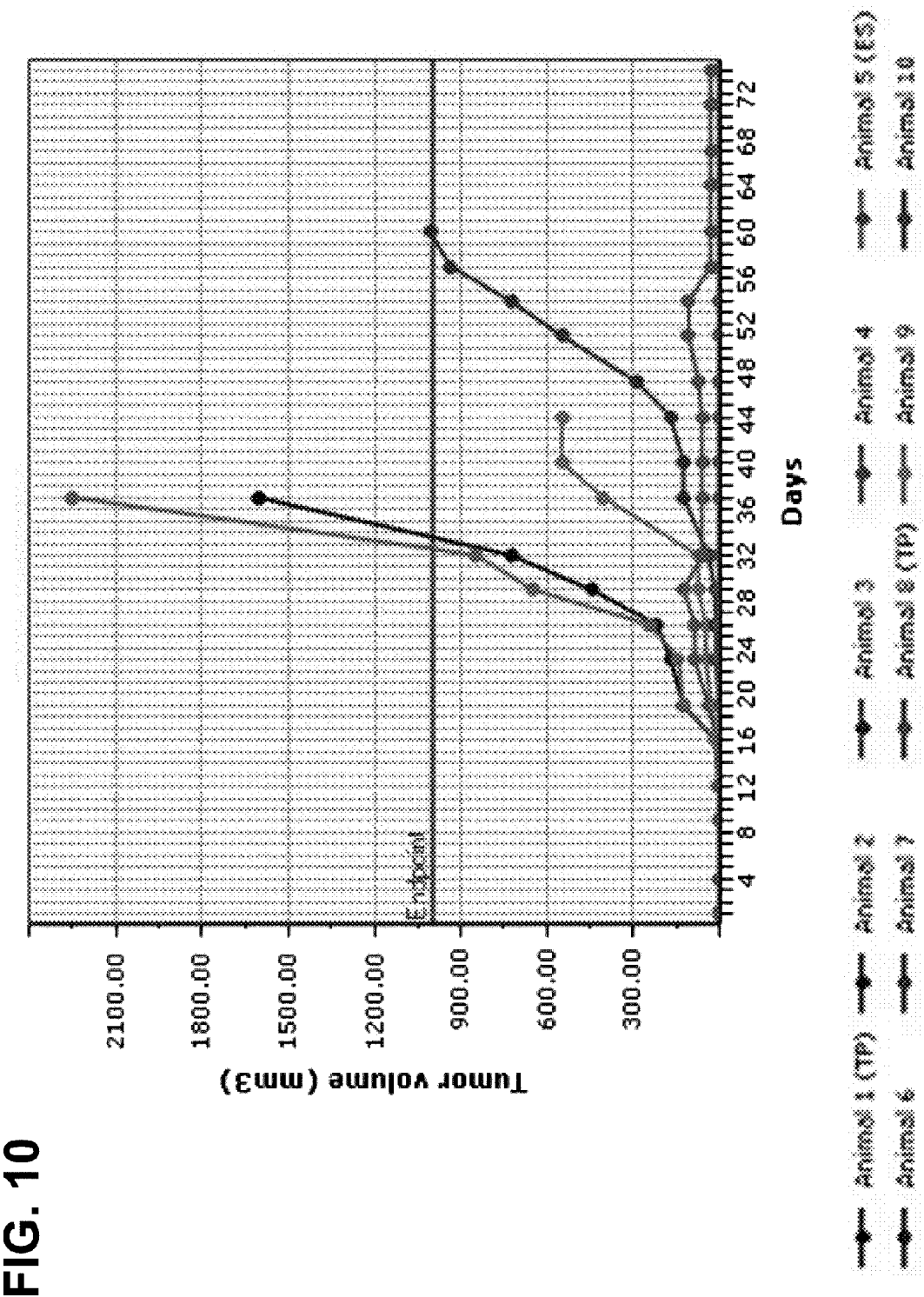
FIG. 10 is a graph showing tumor volume in individual animals from Group 14 during the course of the study. These animals received LPT-723 orally twice per day at 30 mg/kg from day 3 to endpoint and anti-CTLA-4 i.p. (100 µg/animal day 8; 50 µg/animal days 11 and 14).
Figure 11:
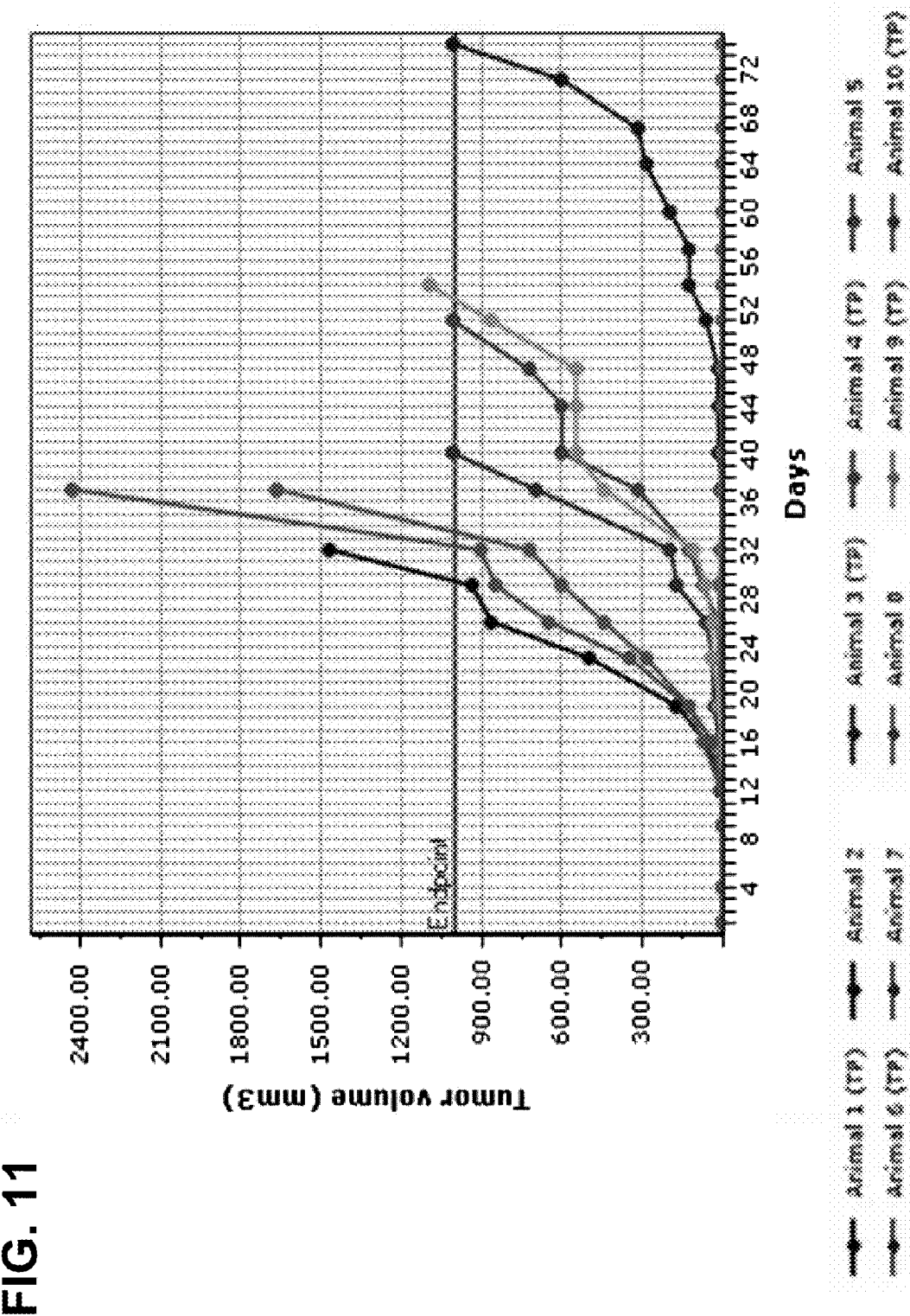
FIG. 11 is a graph showing tumor volume in individual animals from Group 15 during the course of the study. These animals received LPT-723 orally twice per day at 10 mg/kg from day 3 to endpoint and anti-PD-1 i.p. (100 µg/animal biweekly starting day 3).
Figure 12:
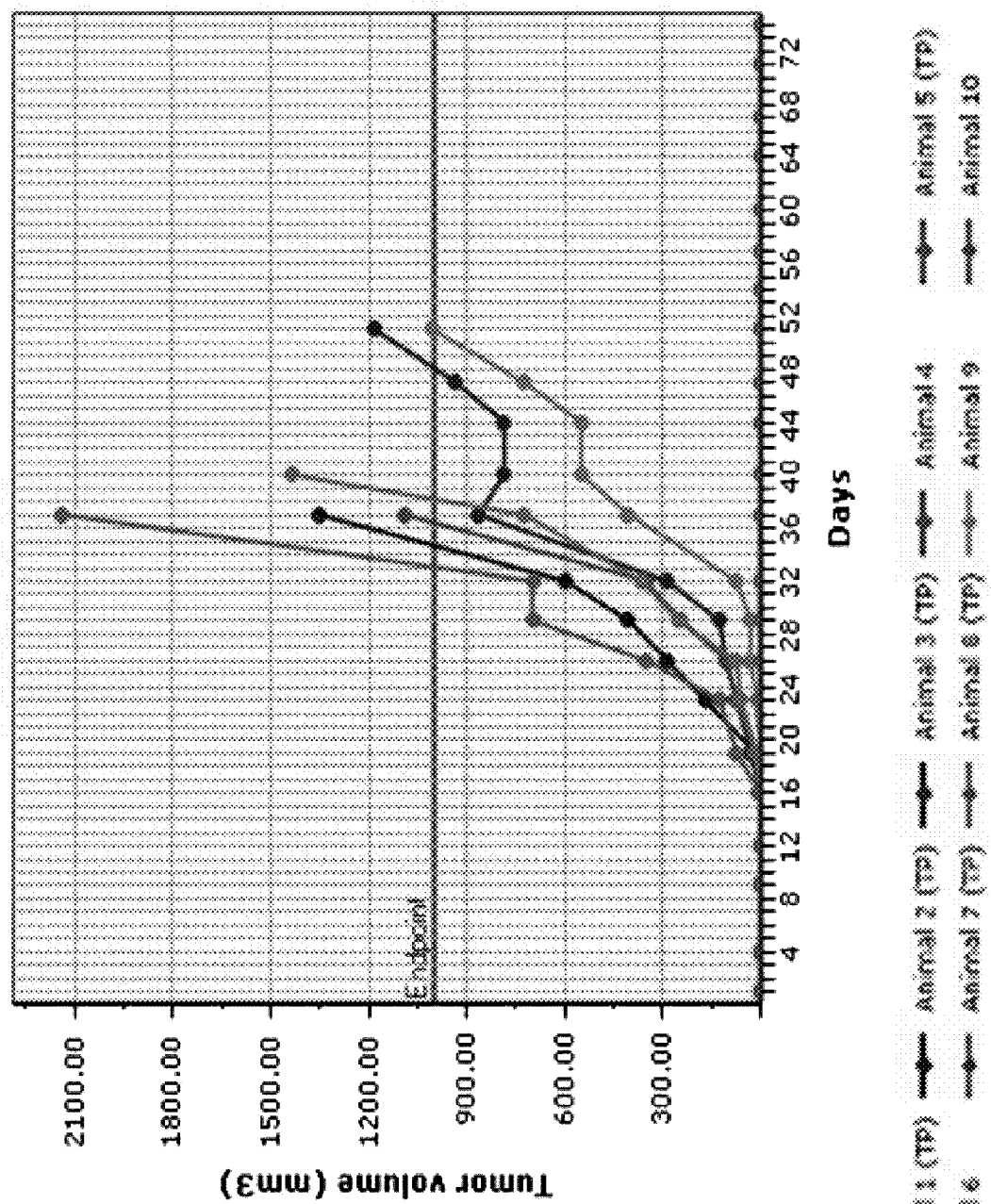
FIG. 12 is a graph showing tumor volume in individual animals from Group 16 during the course of the study. These animals received LPT-723 orally twice per day at 10 mg/kg from day 3 to endpoint and anti-PD-1 i.p. (100 µg/animal biweekly starting day 3).

Very significant synergy was demonstrated in the groups with combinations of LPT-723 (two dose cohorts) and immunotherapy checkpoint inhibitors (PD-1 and CTLA-4 antibodies) showing decreased median tumor volume (FIGS. 1-2) and increased survival (FIG. 3). Body weights ranged from 90-115% of baseline at the end of the study. Median tumor volume for individual mice in control groups 2-4 and LPT-723 monotherapy and combination therapy groups 11-16 are shown in FIGS. 4-12.

Figure 13:
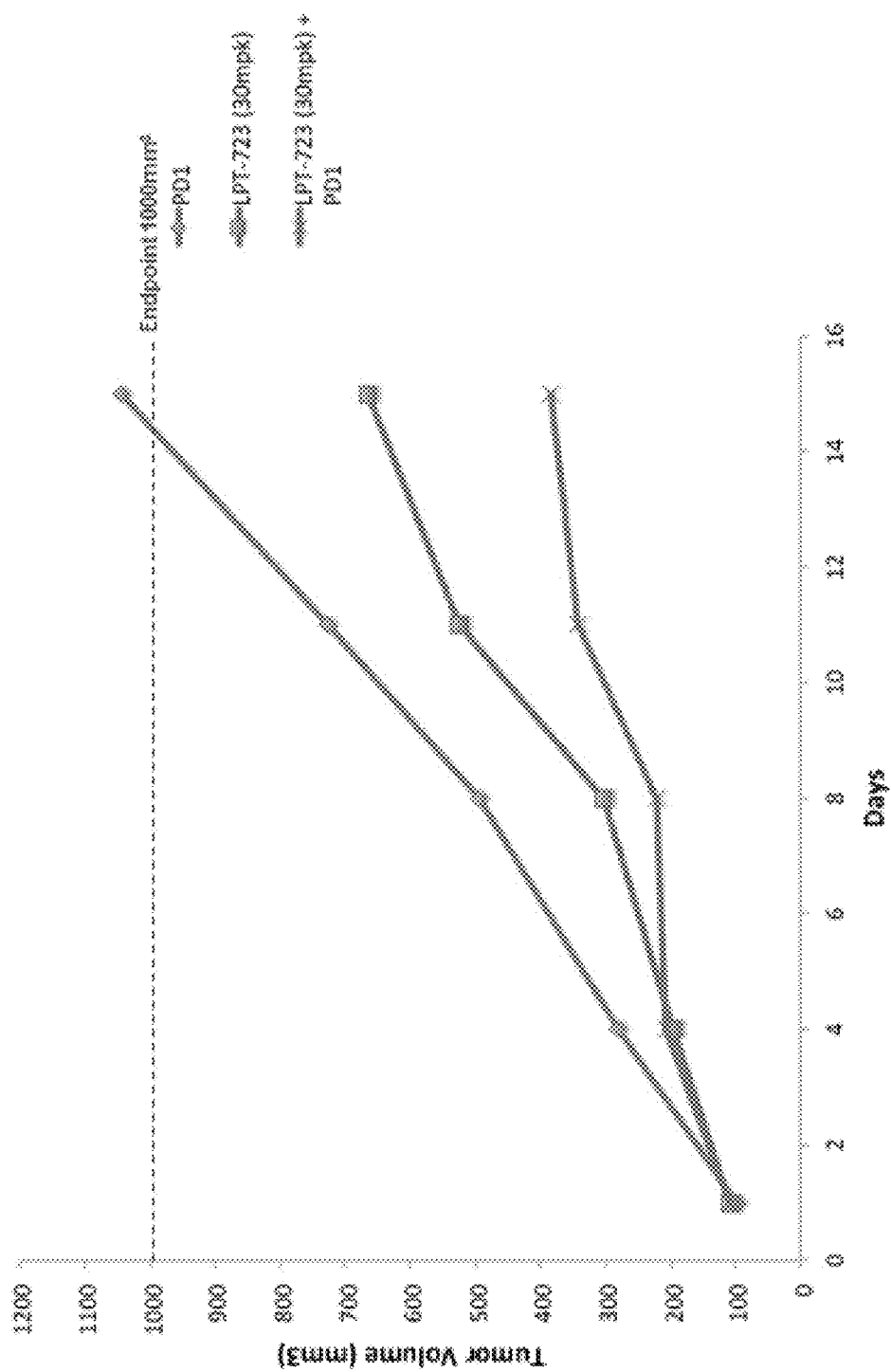
FIG. 13 shows the median tumor volume over 15 days in a therapeutic Colon26 cancer model. The purple line demonstrates the synergistic effect of the combination of LPT-723 (30 mg/kg twice daily starting day 1) and anti-PD-1 antibody. N=10 animals per group.

Therapeutic Colon26 Colon Cancer Model:

CR BALB/c mice bearing Colon26 murine syngeneic colon cancer were treated with control (vehicle), anti-CTLA-4 (clone 9H10), anti-PD-1 (clone RMP1-14), anti-CTLA-4/anti-PD-1 combination, LPT-723 (10 mpk, 30 mpk), anti-CTLA-4/LPT-723 (10 mpk, 30 mpk) combination, anti-PD-1/LPT-723 (10 mpk, 30 mpk) combination, and anti-CTLA-4/anti-PD-1/LPT-723 (10 mpk, 30 mpk) combination. Treatment was initiated when tumor volume reached approximately 80-120 mm³. Anti-CTLA-4 was dosed i.p. on Day 2 at 100 μg/animal and on Days 5 and 8 at 50 μg/animal. Anti-PD-1 was dosed i.p. twice a week for two weeks at 100 μg/animal. LPT-723 was dosed p.o. twice a day starting Day 1. Results are shown for anti-PD-1, LPT-723, and anti-PD-1/LPT-723 combination therapy groups indicating a synergistic effect between LPT-723 and anti-PD-1 (FIG. 13).

Example 2

Figure 14:
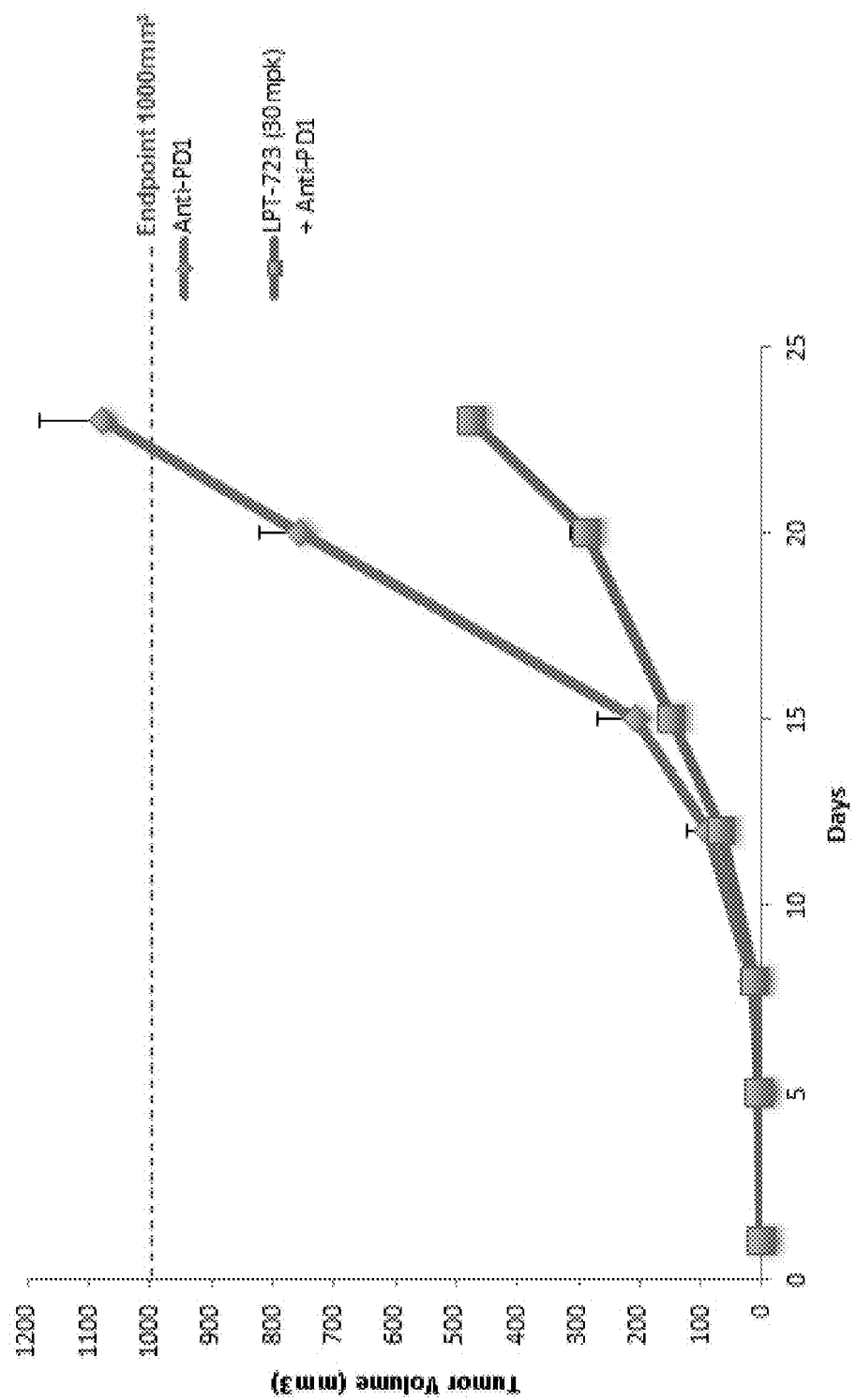
FIG. 14 is a graph of median tumor volume in a Lewis lung cancer (LLC) syngeneic mouse model. LPT-723 (30 mg/kg twice daily starting day 2) combined with anti-PD-1 significantly inhibited tumor growth in comparison with anti-PD-1 alone. N=10 animals per group.

Lewis Lung Cancer (LLC) Model:

C57/BL6 mice were implanted with Lewis Lung murine lung cancer cells on Day 1, and the treatment was initiated on Day 2 with control (vehicle), anti-CTLA-4 (clone 9H10), anti-PD-1 (clone RMP1-14), anti-CTLA-4/anti-PD-1 combination, LPT-723 (10 mpk, 30 mpk), anti-CTLA-4/LPT-723 (10 mpk, 30 mpk) combination, anti-PD-1/LPT-723 (10 mpk, 30 mpk) combination, and anti-CTLA-4/anti-PD-1/LPT-723 (10 mpk, 30 mpk) combination. Anti-CTLA-4 was dosed i.p. on Day 5 at 100 μg/animal and on Days 8 and 11 at 50 μg/animal. Anti-PD-1 was dosed i.p. twice a week for two weeks starting on Day 2 at 100 μg/animal. LPT-723 was dosed p.o. twice a day starting on Day 2. LPT-723 at 30 mpk BID combined with anti-PD-1 (FIG. 14) or anti-CTLA-4 (FIG. 15) significantly inhibited tumor growth in comparison with anti-PD-1 or anti-CTLA-4 alone in the LLC syngeneic mouse model.

Example 3

Pan02 Pancreatic Cancer Model:

C57/BL6 mice bearing Pan02 murine syngeneic pancreatic cancer were treated with control (vehicle), anti-PD-1 (clone RMP1-14), LPT-723 and anti-PD-1/LPT-723 combination. Treatment was initiated when tumor volume reached approximately 80-120 mm³. Anti-PD-1 was dosed i.p. twice a week for three weeks at 10 mpk. LPT-723 was dosed p.o. twice a day at 30 mpk.

LPT-723 monotherapy and combination therapy resulted in greater than 60% decreased median tumor volume in this model (FIG. 16A). No significant changes in body weights were noted. An in vitro cell viability assay (CellTiter-Glo luminescent assay) indicated that LPT-723 does not directly kill Pan02 cells (FIG. 16B, $IC_{50}$ for LPT-723 was 26.57 µM on Pan02 cells versus 1.09 µM for the chemotherapeutic agent Cisplatin).

Example 4

A20 Lymphoma Cancer Model:

BALB/c mice bearing A20 murine syngeneic B cell lymphoma were treated with control (vehicle), anti-PD-1 (clone RMP1-14), LPT-723 and anti-PD-1/LPT-723 combination. Treatment was initiated when tumor volume reached approximately 80-120 mm³. Anti-PD-1 was dosed i.p. twice a week for three weeks at 10 mpk. LPT-723 was dosed p.o. twice a day at 30 mpk. LPT-723 monotherapy resulted in a 43% decrease in median tumor volume and the combination therapy resulted in a 79% decrease at Day 15 (FIG. 17A), indicating a highly synergistic effect of the combination. No significant changes in body weights were noted. An in vitro cell viability assay indicated that LPT-723 does not directly kill A20 cells (FIG. 17B, $IC_{50}$ for LPT-723 was 84.10 µM on A20 cells versus 1.07 µM for Cisplatin).

Example 5

MBT-2 Bladder Cancer Model:

C3H mice bearing MBT-2 murine syngeneic bladder cancer were treated with control (vehicle), anti-PD-1 (clone RMP1-14), LPT-723 and anti-PD-1/LPT-723 combination. Treatment was initiated when tumor volume reached approximately 80-120 mm³. Anti-PD-1 was dosed i.p. twice a week for three weeks at 10 mpk. LPT-723 was dosed p.o. twice a day at 30 mpk. All therapy groups showed at least 70% reduction in median tumor volume compared to control on Day 13 in the MBT-2 model (FIG. 18A). No significant changes in body weights were noted. An in vitro cell viability assay indicated that LPT-723 does not directly kill MBT-2 cells (FIG. 18B, $IC_{50}$ for LPT-723 was 45.49 µM on MBT-2 cells versus 6.867 µM for Cisplatin).

Example 6

HCT-116 Human Colorectal Cancer Xenograft Model:

BALB/c nude mice bearing HCT-116 human colon xenografts were treated with control (vehicle) and LPT-723. Treatment was initiated when tumor volume reached approximately 80-120 mm³. LPT-723 was dosed p.o. twice a day at 30 mpk. LPT-723 monotherapy activity was demonstrated, resulting in a 45% inhibition in tumor growth (FIG. 19A), despite no activity of LPT-723 at doses up to 30 µM in vitro on HCT116 cells in culture (FIG. 19B). The tumor growth inhibition results suggest LPT-723 modulates the tumor stromal microenvironment rather than a direct tumor cell effect.

Example 7

Upstate Kinase Panel:

The inhibitory activity of LPT-723 was determined by following the residual kinase activity of many kinases which were tested either using a radiometric assay, or a spectrophotometric assay. In the radiometric assay, radioactivity incorporated into the protein, phospho-peptide or phospholipid product from $^{33}$P-☐-ATP was followed as a function of time. In the spectrophotometric assay, each mole of ADP produced by the kinase reaction was coupled to the generation of one mole of NAD from NADH using pyruvate kinase and lactate dehydrogenase.

The KinaseProfiler™ (Eurofins Pharma Discovery) assays employed a similar radiometric detection assay. Table 3 below lists the peptide substrate, its concentration, and the ATP concentration used in each kinase assay. The test compounds were introduced as DMSO solutions into the assay. After a specified reaction time, the reaction was quenched and the $^{33}$P-labeled phospho-peptide/protein produced was trapped on a filter and quantified on a radioactivity counter. No toxicity issues were observed.

TABLE 3

| Kinase Assay | ATP (µM) | ATP $K_M$ (µM) | [peptide substrate] | | Substrate |
|---|---|---|---|---|---|
| ABL | 45 | 48 | 50 | µM | EAIYAAPFAKKK |
| ALK | 200 | 229 | 250 | µM | KKKSPGEYVNIEFG |
| AMPKα1 | 90 | 80 | 200 | µM | AMARAASAAALSARRR |
| ASK1 | 200 | 371 | 0.33 | mg/mL | MBP |
| AXL | 90 | 80 | 250 | µM | KKSRGDYMTMQIG |
| BLK | 120 | 125 | 0.1 | mg/mL | polyE4Y |
| BTK | 200 | >200 | 250 | µM | KVEKIGEGTYGVVYK |
| CaMKIIβ | 15 | 22 | 30 | µM | KKLNRTLSV |
| CDK1/CycB | 45 | 51 | 0.1 | mg/mL | Histone H1 |
| CDK5/P35 | 15 | 30 | 0.1 | mg/mL | Histone H1 |

TABLE 3-continued

| | | | | | |
|---|---|---|---|---|---|
| CHK1 | 90 | 84 | 200 | µM | KKKVSRSGLYRSPSMPENLNRPR |
| CK1γ1 | 45 | 38 | 200 | µM | KRRRALS(p)VASLPGL |
| cKIT | 200 | 450 | 0.1 | mg/mL | polyE4Y |
| cRAF | 120 | 120 | 0.66 | mg/mL | MBP |
| cSRC | 45 | 45 | 0.1 | mg/mL | polyE4Y |
| EGFR | 10 | 3 | 0.1 | mg/mL | polyE4Y |
| EphB4 | 10 | 11 | 0.1 | mg/mL | polyE4Y |
| FES | 45 | 50 | 0.1 | mg/mL | polyE4Y |
| FGFR3 | 15 | 28 | 0.1 | mg/mL | polyE4Y |
| Flt1 (VEGFR1) | 200 | 2118 | 250 | µM | KKKSPGEYVNIEFG |
| FYN | 70 | 64 | 250 | µM | KVEKIGEGTYGVVYK |
| HIPK2 | 10 | 10 | 0.33 | mg/mL | MBP |
| IGF-1R | 200 | >200 | 250 | µM | KKKSPGEYVNIEFG |
| IKKα | 10 | 6 | 250 | µM | KKKKERLLDDRHDSGLDSMKDEE |
| IR | 200 | 447 | 250 | µM | KKSRGDYMTMQIG |
| JNK1α1 | 45 | 41 | 3 | µM | ATF2 |
| LCK | 90 | 90 | 250 | µM | KVEKIGEGTYGVVYK |
| LYN | 70 | 79 | 0.1 | mg/mL | polyE4Y |
| MAPK1 | 70 | 67 | 250 | µM | PRELVEPLTPSGEAPNQALLR |
| MEK1 | 10 | ND | 1 | µM | inactive MAPK2 |
| MKK6 | 10 | ND | 1 | µM | inactive SAPK2a |
| MKK7β | 10 | ND | 2 | µM | inactive JNK1a1 |
| MLCK | 70 | 70 | 250 | µM | KKLNRTLSFAEPG |
| MSK1 | 90 | 76 | 30 | µM | GRPRTSSFAEGKK |
| MST2 | 155 | 165 | 0.33 | mg/mL | MBP |
| mTOR | 70 | 70 | 2 | mg/mL | mTOR substrate |
| NEK2 | 120 | 120 | 0.33 | mg/mL | MBP |
| PAK2 | 90 | 89 | 30 | µM | KEAKEKRQEQIAKRRRLSSLRAST-SKSGGSQK |
| PDGFRα | 120 | 106 | 0.1 | mg/mL | polyE4Y |
| Pim-2 | 15 | 15 | 300 | µM | RSRHSSPYAGT |
| PKCβII | 70 | 58 | 0.1 | mg/mL | Histone H1 |
| PKCs | 155 | 170 | 50 | µM | ERMRPRKRQGSVRRRV |
| PKCθ | 15 | 16 | 0.1 | mg/mL | Histone H1 |
| PRAK | 15 | 18 | 30 | µM | KKLRRTLSVA |
| PRK2 | 15 | 10 | 30 | µM | AKRRRLSSLRA |
| RET | 70 | 58 | 250 | µM | KKKSPGEYVNIEFG |
| RIPK2 (RICK) | 120 | 133 | 0.33 | mg/mL | MBP |
| ROCK II | 15 | 22 | 30 | µM | KEAKEKRQEQIAKRRRLSSLRAST-SKSGGSQK |
| ROS (KROS) | 200 | 563 | 250 | µM | KKKSPGEYVNIEFG |

TABLE 3-continued

| | | | | | |
|---|---|---|---|---|---|
| RSK3 | 10 | 7 | 30 | µM | KKKNRTLSVA |
| SAPK2β | 45 | 58 | 0.33 | mg/mL | MBP |
| SGK | 90 | 93 | 30 | µM | GRPRTSSFAEGKK |
| TAK1 | 45 | 45 | 2 | mg/mL | casein |
| TIE2 | 200 | 439 | 0.1 | mg/mL | polyE4Y |
| TrkA | 120 | 129 | 250 | µM | KKKSPGEYVNIEFG |
| ZAP70 | 15 | 15 | 0.1 | mg/mL | polyE4Y |

| Substrate | SEQ ID NO. |
|---|---|
| EAIYAAPFAKKK | SEQ ID NO.: 1 |
| KKKSPGEYVNIEFG | SEQ ID NO.: 2 |
| AMARAASAAALARRR | SEQ ID NO.: 3 |
| KKSRGDYMTMQIG | SEQ ID NO.: 4 |
| KVEKIGEGTYGVVYK | SEQ ID NO.: 5 |
| KKLNRTLSVA | SEQ ID NO.: 6 |
| KKKVSRGLYRSPSMPENLNRPR | SEQ ID NO.: 7 |
| KRRRALS(p)VASLPGL | SEQ ID NO.: 8 |
| KKKKERLLDDRHDSGLDSMKDEE | SEQ ID NO.: 9 |
| RRELVEPLTPSGEAPNQALLR | SEQ ID NO.: 10 |
| KKLNRTLSFAEPG | SEQ ID NO.: 11 |
| GRPRTSSFAEGKK | SEQ ID NO.: 12 |
| KEAKEKRQEQIAKRRRLSSLRASTSKSGGSQK | SEQ ID NO.: 13 |
| RSRHSSYPAGT | SEQ ID NO.: 14 |
| ERMRPRKRQGSVRRRV | SEQ ID NO.: 15 |
| AKRRRLSSLRA | SEQ ID NO.: 16 |

Example 8

2-Strain Ames Test:

Test System:

The two tester strains used were the *Salmonella typhimurium* histidine auxotrophs TA98 and TA100 as described by Ames et al. (1975). Tester strain TA98 is reverted from auxotrophy to prototrophy by frameshift mutagens while tester strain TA100 is reverted by mutagens that cause both frameshift and base pair substitution mutations.

Experimental Design:

The test system was exposed to LPT-723 via the plate incorporation methodology originally described by McCann et al. (1975) and updated by Maron and Ames (1983). Briefly, LPT-723 was tested at eight dose levels along with appropriate vehicle control and positive controls. Overnight cultures of tester strains TA98 and TA100 were plated on selective minimal agar in the presence and absence of Aroclor-induced rat liver S9. All dose levels of LPT-723, vehicle controls and positive controls were plated in duplicate.

Plating and Scoring Procedures:

LPT-723 dilutions were prepared immediately before use and delivered to the test system at room temperature under yellow light. One-half (0.5) milliliter of S9 or Sham mix, 100 µL of tester strain and 50 µL of vehicle or LPT-723 dilution were added to 2.0 mL of molten selective top agar at 45±2° C. After vortexing, the mixture was overlaid onto the surface of 25 mL of minimal bottom agar. When plating the positive controls, the LPT-723 aliquot was replaced by a 50 µL aliquot of appropriate positive control. After the overlay had solidified, the plates were inverted and incubated for approximately 48 to 72 hours at 37±2° C. Plates were counted immediately following the incubation period or were stored at 2-8° C. until colony counting could be conducted.

The condition of the bacterial background lawn was evaluated for evidence of LPT-723 toxicity using a dissecting microscope. Precipitate was evaluated by visual examination without magnification. Revertant colonies for each tester strain and activation condition were counted either entirely by automated colony counter or entirely by hand unless the plate exhibited toxicity. Plates with sufficient LPT-723 precipitate to interfere with automated colony counting were counted manually.

Solubility and Dose Levels Tested:

Dimethyl sulfoxide (DMSO) was selected as the solvent of choice based on compatibility with the target cells. The LPT-723 formed solutions in dimethyl sulfoxide (DMSO) from 0.03 to 100 mg/mL. The maximum dose tested was 5000 μg per plate, which dose was achieved using a concentration of 100 mg/mL and a 50 μL plating aliquot. Dose levels tested were 1.5, 5.0, 15, 50, 150, 500, 1500 and 5000 μg per plate. No toxicity was observed.

Example 9

Micronucleus Assay:

Prior to necropsy on Day 8, rats in a main study group of a 7-day oral toxicity and toxicokinetic (TK) study were bled from the jugular vein for the evaluation of the flow analysis of micronucleus. No toxicity was observed. The procedure used for collection and fixation of blood is summarized below:

Preparation of the Fixative Tubes:

Fixative tubes were prepared one day prior to blood collection. Two 15 mL polypropylene centrifuge tubes (VWR no. 21008-103) were required per sample. 2 mL of ultracold fixative-methanol was added to each appropriately labeled tube (Tubes B1 and B2), and caps were replaced. The rack of tubes was placed overnight at approximately −80° C. to allow for sufficient chilling of the fixative.

Preparation of the Anticoagulant/Diluent Vials (Prior to Blood Collection):

One vial (2 mL cryovials; VWR no. 66008-728) was required for each sample. 350 μL of anticoagulant/diluent (Prototype Pig-a Mutation Assay Anticoagulant Solution, lot #17716, provided by BioReliance, from Litron) was aseptically aliquoted into each appropriately labeled vial (Tube A). The vials were refrigerated (2-8° C.) until needed.

Collection of Blood Samples:

Approximately 0.3 mL of blood was collected from each animal into $K_2$EDTA tubes. The tubes were mixed well by inversion and placed on wet ice for a maximum of 30 minutes before proceeding. A volume of approximately 100 μL (60 to 120 μL was required) of blood was transferred from the $K_2$EDTA tube and placed into the tube containing the cold anticoagulant (Tube A). The tubes containing the anticoagulant and blood (Tube A) were mixed gently by inversion and were kept on wet ice for a maximum of 30 minutes before fixing.

Fixing the Samples:

It was extremely important that the tubes containing the fixative and fixed blood remain ultra-cold (approximately −80° C.) and did not come in contact with vapors from dry ice. $CO_2$ vapor causes carbonation and cellular aggregation. For this same reason, the fixative was not stored in a freezer containing dry ice, and fixation was not performed on dry ice. To avoid this problem, tubes containing the fixative were taken directly from the freezer. The fixative was kept in an ultracold (approximately −80° C.) freezer. The following steps were performed very quickly (in less than one minute) and were performed near the freezer. Each sample was fixed in duplicate. Duplicate (backup) samples are important in the event of shipping complications or if flow cytometric analysis problems arise.

Immediately prior to fixing, the vial containing the blood/anticoagulant mixture (Tube A) was inverted to ensure a homogeneous suspension. Using a micropipettor, 180 μL of blood was transferred from Tube A into each of the duplicate tubes (Tubes B1 and B2) containing the ultra-cold fixative-methanol. The tip of the pipettor was held approximately 1 cm above the fixative. Making sure that the pipette tip did not touch the side of the tube or the surface of the fixative, the 180 μL of diluted blood sample was forcefully dispensed directly into the fixative. The tube of fixed blood was capped tightly and vortexed briefly (only 3 to 5 seconds) and returned to the ultra-cold freezer (approximately −80° C.). The samples were stored at approximately −80° C. (in a freezer where no dry ice was stored) until shipment. Samples (in Tubes B1 and 62) stored in the fixative at −70° C. or below are stable for at least 1 year, as long as temperature is maintained. Remaining blood in the 2 mL cryovials (Tube A) containing cold anticoagulant was discarded.

Transferring of Fixed Samples into LTSS:

Samples were transferred into LTSS after they had been in the fixative for at least 3 days. Each cryovial was labeled appropriately. The buffer solution was packed on ice to achieve ice-cold, but not freezing, temperature (approximately 45 minutes). With a container of ice and a 25 mL pipette ready for aliquoting the buffer solution used below, the following steps were performed as quickly as possible (within approximately 20 seconds). A tube of fixed blood sample (Tubes B1 and B2) was removed from the ultra-cold freezer. The capped tube was quickly placed on ice and the freezer was closed. The tube was vortexed for 3 to 5 seconds to resuspend the cells and the cap was loosened on the tube. 12 mL of ice-cold buffer solution was immediately added to each tube. Care was taken not to touch the tube with the pipette tip to prevent transfer of sample from one tube to another. The caps were tightened, the tubes inverted once to mix the solutions, and the tubes were immediately placed on ice until all were processed. Once the buffer solution had been added to the fixed cells, it was important that the tubes remained on ice or at 2° C. to 8° C. The tubes were centrifuged at approximately 300×g to 400×g for 5 minutes. When centrifugation was completed, the tubes were quickly removed and immediately replaced on ice. The supernatant from each tube was aspirated, leaving less than 50 μL of supernatant in which to resuspend cells. Tubes were recapped and immediately returned to ice. Working with one sample at a time, the cells were quickly resuspended in the remaining supernatant by vortexing. The tube was placed back on ice and the remaining samples were resuspended. 1 mL of long term storage solution (LTSS) (provided by BioReliance) was added to each tube, and the content was transferred into the appropriate cryovial and the caps were tightened. The samples were stored at approximately −80° C. pending shipment. Test results revealed no significant toxicity.

Example 10

Monkey Cardiovascular (CV) Studies:

Vehicle and LPT-723 Preparation & Experimental Design:

The vehicle, 2% TPGS/1.5% HPMCAS-HF/1.5% PVP-VA with 50 mM pH 5.0 sodium citrate (in deionized water), was pre-formulated and was dispensed for use on each day of dosing. The vehicle was stored stirring at room temperature in an amber glass container until acquired for dosing.

The test article LPT-723 was formulated as a 25% drug loaded spray dried dispersion with 75% of HPMC-AS as the inert excipient. Thus, test article formulation concentrations were calculated as the free base using a correction factor of 4. No adjustment was made for purity. Appropriate amounts of the LPT-723 were mixed with the vehicle to achieve nominal concentrations of 5 and 8 mg/mL. Formulations of LPT-723 were prepared on each day of dosing as needed and were stored stirring at room temperature in an amber glass container until acquired for dosing.

Vehicle and LPT-723 Administration:

The same three or four male monkeys were administered vehicle (0 mg/kg) and LPT-723 at dose levels of 25 and 40 mg/kg via oral gavage at a dose volume of 5 mL/kg (Table 4 below). All doses were administered according to a cross-over design, with one or two animals/dose level being dosed on each occasion with a 7 or 14-day washout period between administrations. Animal number 6002 was not dosed at 25 mg/kg due to the animal's transmitter no longer functioning properly. The formulations were stirred throughout dose administration. After each dose and prior to removal of the gavage tube, the tube was flushed with 10 mL of tap water. All cardiovascular and body temperature post-dose data were based on the tap water flush. Individual doses were based on the most recent body weights. There were no significant toxicological observations.

TABLE 4

Experimental Design

| Dose Group | Dose Level (mg/kg) | Number of Male Animals[a] |
|---|---|---|
| 1 | 0 | 4 |
| 2 | 25 | 3[b] |
| 3 | 40 | 4 |

Dosing Schedule

| Animal Number | Dose level (mg/kg) | | |
|---|---|---|---|
| | 0 | 25 | 40 |
| 6001 | Days 1 and 22 | Day 29 | Day 8 |
| 6002 | Days 1 and 22 | NA | Day 8 |
| 6003 | Days 8 and 29 | Day 22 | Day 1 |
| 6004 | Days 8 and 29 | Day 22 | Day 1 |

[a]Each dose group was administered to the same 3 or 4 animals according to a cross-over design with at least a 7-day washout between each dose.
[b]Animal number 6002 was not dosed at 25 mg/kg due to a nonfunctional transmitter.
NA—Not applicable Example 11

Rat 28-Day GLP Toxicity Study:

Vehicle and Test Article Preparation:

The vehicle, 2% TPGS/1.5% HPMCAS-HF/1.5% PVP-VA with 50 mM pH 5.0 sodium citrate in deionized water, was prepared for use weekly and was stored at room temperature when not in use. A correction factor of 4 was used to adjust for purity when preparing the LPT-723 formulations. Appropriate amounts of the LPT-723 were mixed with the vehicle to achieve nominal concentrations of 0.3, 0.6, and 1.2 mg/mL. Formulations of the LPT-723 were prepared daily, stored at room temperature, protected from light, and were dosed within 4 hours of preparation.

Animal Acquisition and Acclimation:

A total of 98 male and 98 female CD® [Crl:CD® (SD)] rats (approximately 6 to 7 weeks of age at receipt) were received from Charles River Laboratories, Portage, Mich. During the 10-day acclimation period, the animals were observed daily with respect to general health and any signs of disease. All animals were given a detailed clinical examination prior to selection for study. The animals were administered a sham dose of tap water on two occasions in the same manner and dose volume intended for use on study.

Randomization, Assignment to Study, and Maintenance:

Using a standard, by weight, measured value randomization procedure, 85 male and 85 female animals (weighing 228 to 283 g and 170 to 218 g, respectively, at randomization) were assigned to the control and treatment groups identified in the following table.

TABLE 5

Group Assignments

| Group Number | Dose Level (mg/kg/day) | Number of Animals | |
|---|---|---|---|
| | | Male | Female |
| Main Study | | | |
| 1 | 0 | 15[a] | 15[a] |
| 2 | 3 | 15[a] | 15[a] |
| 3 | 6 | 15[a] | 15[a] |
| 4 | 12 | 15[a] | 15[a] |
| Toxicokinetic | | | |
| 5 | 0 | 4[b] | 4[b] |
| 6 | 3 | 7[b] | 7[b] |
| 7 | 6 | 7[b] | 7[b] |
| 8 | 12 | 7[b] | 7[b] |

[a]Five animals were maintained on study for a 4-week recovery peiod.
[b]One additional animal was included as a possible replacement animal.

Vehicle and LPT-723 Administration:

Vehicle and LPT-723 were administered once daily for 22 days for main study animals at 12 mg/kg/day, for 23 days for TK animals at 12 mg/kg/day, and for 28 days for all animals at 0, 3, and 6 mg/kg/day. The animals were dosed via oral gavage at a dose volume of 10 mL/kg. The control group received the vehicle in the same manner as the treated groups. The vehicle and test article were dosed from stirred formulations at approximately the same time each day (±2 hours) based on the first animal dosed each day. Individual doses were based on the most recent body weights.

Results:

The no observed adverse effect level (NOAEL) was <3 mg/kg. AUC was approximately 35 and therapeutic index was <4. The compound was poorly tolerated in rats: several clinical chemistry parameters were effected, most notably there was a large increase in circulating neutrophils. The increased neutrophil count correlated with tissue accumulation and an inflammatory state in multiple organs, particularly the gastrointestinal tract.

Example 12

Monkey 7-Day Dose Range Finding Study:

Preparation of the Control/Vehicle Item:

The control/vehicle item (2% TPGS/1.5% HPMCAS-HF/1.5% PVP-VA with 50 mM sodium citrate buffer pH 5.0) was prepared 3 days prior to the start of dosing and was stored at room temperature, away from direct light for the duration of the study. The instructions below were for the preparation of a final volume of 2.5 L. These instructions were scaled as needed.

500 mL of 10% Vitamin E-TPGS were added to an appropriate sized container and stirring was initiated. 750 mL of 5% HPMCAS-HF/5% PVP-VA were added to the same container and stirred at medium speed for 30 minutes to ensure proper mixing. 1 L of deionized water was added and stirring was continued for 30 minutes. 125 mL of 1M sodium citrate buffer and 125 mL of deionized water were added with stirring. The final vehicle was stirred at medium speed for 1 hour. The vehicle was a hazy solution and was stored at room temperature, away from direct light for the duration of the study.

Experimental Design:

The test and control/vehicle items were administered once daily for 7 consecutive days by oral gavage as described in Table 6 below. The dose volume administered to each animal was 5 mL/kg. One day after the end of dosing, the Main animals were euthanized and subjected to a necropsy examination on Day 8.

TABLE 6

| Group Numbers | Group Designation | Dose Level (mg/kg/day) | Dose Concentration (mg/mL) | Dose Volume (mL/kg) | Main Animals Male | Main Animals Female |
|---|---|---|---|---|---|---|
| 1 | Control* | 0 | 0 | 5 | 2 | 2 |
| 2 | Low Dose | 15 | 3 | 5 | 2 | 2 |
| 3 | Mid Dose | 25 | 5 | 5 | 2 | 2 |
| 4 | High Dose | 40 | 8 | 5 | 2 | 2 |

*The Control animals received the control/vehicle item (2% TPGS/1.5% HPMCAS-HF/1.5% PVP-VA with 50 mM sodium citrate buffer pH 5.0) alone.
**Dose level and concentration are expressed in terms of active test item; consequently a correction factor of 4 was used when weighing and dispensing the test item powder. LPT-723, was used as a spray dried dispersion (SDD) containing 25% active and 75% HPMCAS-HF polymer.

Results:

The highest dose of LPT-723 exceeded the maximum tolerated dose (MTD). There was a dose-related decrease in lymphocyte counts with concomitant effects in bone marrow and lymphoid tissues. Assuming a NOAEL at approximately 50 AUC, the expected therapeutic index would be approximately 5 with lower doses.

Example 13

Mouse 7-Day Dose Range Finding Study:

Preparation of Test and Control/Vehicle Items:

Vehicle is 2% TPGS/1.5% HPMCAS-HF/1.5% PVP-VA with 50 mM sodium citrate (pH 5.0) in deionized water. LPT-723 is a spray dried dispersion (SDD) containing 25% active and 75% HPMCAS-HF polymer. Test and vehicle items were stored at room temperature, protected from light, and desiccated. Dose formulation was prepared daily. Unless indicated otherwise, LPT-723 was mixed with vehicle to achieve the desired concentrations, using appropriate mixing equipment to achieve homogenous formulations.

The LPT-723 and vehicle were administered once per day for 7 consecutive days. Doses were administered at approximately the same time (±2 hours) throughout the duration of the study. All main study animals were submitted for necropsy on Day 8 (the day following the final dose). See Table 7 below.

Results:

LPT-723 was well tolerated, with a decrease in lymphocyte and monocyte counts. There were no clinical signs or histopatholoy findings. This study provided additional mitigation of the apparently "rat specific" findings reported in Example 11.

CITED DOCUMENTS

Brahmer J R, et al. Safety and activity of anti-PD-L1 antibody in patients with advanced cancer. N Engl J Med. 2012 Jun. 28; 366(26):2455-65.

Bronte V, et al. Identification of a CD11b(+)/Gr-1(+)/CD31 (+) myeloid progenitor capable of activating or suppressing CD8(+) T cells. Blood. 2000 Dec. 1; 96(12):3838-46.

Bunt S K, et al. Inflammation induces myeloid-derived suppressor cells that facilitate tumor progression. J Immunol. 2006 Jan. 1; 176(1):284-90.

Cleary J M, Shapiro G I. Development of phosphoinositide-3 kinase pathway inhibitors for advanced cancer. Curr Oncol Rep. 2010 March; 12(2):87-94.

Du R, et al. HIF1alpha induces the recruitment of bone marrow-derived vascular modulatory cells to regulate tumor angiogenesis and invasion. Cancer Cell. 2008 March; 13(3):206-20.

Grivennikov S I, et al. Immunity, inflammation, and cancer. Cell. 2010 Mar. 19; 140(6):883-99.

TABLE 7

| Group | Number of Animals Male | Treatment | Dose Level[B] (mg/kg/day) | Dose Conc.[B] (mg/mL) | Dose Volume (mL/kg/day) | Necropsy (Day 8) Male |
|---|---|---|---|---|---|---|
| Main Study Animals ||||||| 
| 1 | 6 | Vehicle[A] | 0 | 0 | 10 | 6 |
| 2 | 6 | VRT-1098813 | 15 | 1.5 | | 6 |
| 3 | 6 | VRT-1098813 | 35 | 3.5 | | 6 |
| 4 | 6 | VRT-1098813 | 70 | 7 | | 6 |
| Toxicokinetic Animals ||||||| 
| 5 | 18 | VRT-1098813 | 15 | 1.5 | 10 | — |
| 6 | 18 | VRT-1098813 | 35 | 3.5 | | — |
| 7 | 18 | VRT-1098813 | 70 | 7 | | — |

Conc.—concentration
[A]Control animals received vehicle: 2% TPGS/1.5% HPMCAS-HF/1.5% PVP-VA with 50 mM sodium citrate (pH 5.0) in deionized water
[B]Dose level and concentration are expressed in terms of active test item. A correction factor of 4.0 was used when weighing and dispensing the LPT-723 powder. The test item, LPT-723 was used as a spray dried dispersion (SDD) containing 25% active and 75% HPMCAS-HF polymer.

Hodi F S, et al. Improved survival with ipilimumab in patients with metastatic melanoma. N Engl J Med. 2010 Aug. 19; 363(8):711-23.

Kim K, et al. Eradication of metastatic mouse cancers resistant to immune checkpoint blockade by suppression of myeloid-derived cells. Proc Natl Acad Sci USA. 2014 Aug. 12; 111(32):11774-9.

Kim S, et al. Carcinoma-produced factors activate myeloid cells through TLR2 to stimulate metastasis. Nature. 2009 Jan. 1; 457(7225):102-6.

Korman A J, et al. Checkpoint blockade in cancer immunotherapy. Adv Immunol. 2006; 90:297-339.

Lin E Y, et al. Macrophages regulate the angiogenic switch in a mouse model of breast cancer. Cancer Res. 2006 Dec. 1; 66(23):11238-46.

Maron D M, Ames B N. Revised methods for the *Salmonella* mutagenicity test. Mutat Res. 1983 May; 113(3-4):173-215.

McCann J, et al. Detection of carcinogens as mutagens in the *Salmonella*/microsome test: assay of 300 chemicals. Proc Natl Acad Sci USA. 1975 December; 72(12):5135-9.

Nagaraj S, et al. Reciprocal relationship between myeloid-derived suppressor cells and T cells. J Immunol. 2013 Jul. 1; 191(1):17-23.

Pardoll D M. The blockade of immune checkpoints in cancer immunotherapy. Nat Rev Cancer. 2012 Mar. 22; 12(4): 252-64.

Schmid M C, et al. Receptor tyrosine kinases and TLR/IL1Rs unexpectedly activate myeloid cell PI3kγ, a single convergent point promoting tumor inflammation and progression. Cancer Cell. 2011 Jun. 14; 19(6):715-27.

Talmadge J E, Gabrilovich D I. History of myeloid-derived suppressor cells. Nat Rev Cancer. 2013 October; 13(10): 739-52.

Topalian S L, et al. Safety, activity, and immune correlates of anti-PD-1 antibody in cancer. N Engl J Med. 2012 Jun. 28; 366(26):2443-54.

Wolchok J D, et al. Nivolumab plus ipilimumab in advanced melanoma. N Engl J Med. 2013 Jul. 11; 369(2):122-33.

All patents, patent applications, and publications cited above are incorporated herein by reference in their entirety as if recited in full herein.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for treating or ameliorating the effects of cancer in a subject comprising administering to the subject an effective amount of a first agent, wherein the first agent is a selective PI3Kγ inhibitor or pharmaceutically acceptable salt thereof, and a second agent, wherein the second agent is an immune checkpoint inhibitor.

2. The method according to claim 1, wherein the immune checkpoint inhibitor is selected from a group consisting of an anti-PD-1 antibody, an anti PD-L1 antibody, an anti-CTLA-4 antibody, and combinations thereof.

3. The method according to claim 1, wherein the immune checkpoint inhibitor is selected from a group consisting of nivolumab (Bristol-Myers Squibb), pembrolizumab (Merck), pidilizumab (Curetech), AMP-224 (GlaxoSmithKline/Amplimmune), MPDL3280A (Roche), MDX-1105 (Medarex, Inc./Bristol Myer Squibb), MEDI-4736 (Medimmune/AstraZeneca), arelumab (Merck Serono), ipilimumab (YERVOY, (Bristol-Myers Squibb), tremelimumab (Pfizer), pidilizumab (CureTech, Ltd.), IMP321 (Immutep S.A.), MGA271 (Macrogenics), BMS-986016 (Bristol-Meyers Squibb), lirilumab (Bristol-Myers Squibb), urelumab (Bristol-Meyers Squibb), PF-05082566 (Pfizer), IPH2101 (Innate Pharma/Bristol-Myers Squibb), MEDI-6469 (MedImmune/AZ), CP-870,893 (Genentech), Mogamulizumab (Kyowa Hakko Kirin), Varlilumab (CellDex Therapeutics), Avelumab (EMD Serono), Galiximab (Biogen Idec), AMP-514 (Amplimmune/AZ), AUNP 12 (Aurigene and Pierre Fabre), Indoximod (NewLink Genetics), NLG-919 (NewLink Genetics), INCB024360 (Incyte) and combinations thereof.

4. The method according to claim 1, wherein the first and second agents are administered as a single unit dose.

5. The method according to claim 1, wherein the first and second agents are co-administered.

6. The method according to claim 1, wherein the first agent is administered prior to the second agent.

7. The method according to claim 1, wherein the second agent is administered prior to the first agent.

8. The method according to claim 1, wherein the administration of the first and second agents to the subject provides a synergistic effect in the treatment of the cancer.

9. The method according to claim 1, wherein the cancer is selected from the group consisting of bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, multiple myeloma, neuroblastoma, neuroendocrine cancer, ovarian cancer, pancreatic cancer, prostate cancer, rectal cancer, renal cell carcinoma, rhabdoid cancer, sarcomas, and urinary track cancer.

10. The method according to claim 1, wherein the cancer is selected from the group consisting of bladder cancer, colon cancer, lung cancer, lymphoma, and pancreatic cancer.

11. The method according to claim 1, wherein the subject is a mammal.

12. The method according to claim 11, wherein the mammal is selected from the group consisting of humans, primates, farm animals, and domestic animals.

13. The method according to claim 12, wherein the mammal is a human.

14. The method according to claim 1, wherein the selective PI3Kγ inhibitor is effective to reduce PI3Kγ kinase activity on one or more of the following protein substrates: ABL, ALK, AMPKα1, ASK1, AXL, BLK, BTK, CaMKIIβ, CDK1/CycB, CDEK5/P35, CHK1, CK1γ1, cKIT, cRAP, cSRC, EGFR, EphB4, FES, FGFR3, Flt1 (VEGFR1), FYN, HIPK2, IGF-1R, IKKα, IR, JNK1α,1, LCK, LYN, MAPK1, MEK1, MKK6, MKK7β, MLCK, MSK1, MST2, mTOR, NEK2, PAK2, PDGFRα, Pim-2, PKCβII, $PKC_1$, PKCθ, PRAK, PRK2, RET, RIPK2 (RICK), ROCK II, ROS (KROS), RSK3, SAPK2β, SGK, TAK1, TIE2, TrkA, and ZAP70.

* * * * *

SEQUENCE LISTING

```
<160> NUMBER OF SEQ ID NOS: 16

<210> SEQ ID NO 1
<211> LENGTH: 12
<212> TYPE: PRT
<213> ORGANISM: Artificial Sequence
<220> FEATURE:
<223> OTHER INFORMATION: Peptide Substrate

<400> SEQUENCE: 1

Glu Ala Ile Tyr Ala Ala Pro Phe Ala Lys Lys Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Peptide Substrate

<400> SEQUENCE: 2

Lys Lys Lys Ser Pro Gly Glu Tyr Val Asn Ile Glu Phe Gly
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Peptide Substrate

<400> SEQUENCE: 3

Ala Met Ala Arg Ala Ala Ser Ala Ala Ala Leu Ala Arg Arg Arg
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Peptide Substrate
```

```
<400> SEQUENCE: 4

Lys Lys Ser Arg Gly Asp Tyr Met Thr Met Gln Ile Gly
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Peptide Substrate

<400> SEQUENCE: 5

Lys Val Glu Lys Ile Gly Glu Gly Thr Tyr Gly Val Val Tyr Lys
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: Peptide Substrate

<400> SEQUENCE: 6

Lys Lys Leu Asn Arg Thr Leu Ser Val Ala
1               5                   10

<210> SEQ ID NO 7
<211> LENGTH: 23
<212> TYPE: PRT
<213> ORGANISM: Artificial Sequence
<220> FEATURE:
<223> OTHER INFORMATION: Peptide Substrate

<400> SEQUENCE: 7

Lys Lys Lys Val Ser Arg Ser Gly Leu Tyr Arg Ser Pro Ser Met Pro
1               5                   10                  15

Glu Asn Leu Asn Arg Pro Arg
            20

<210> SEQ ID NO 8
<211> LENGTH: 14
<212> TYPE: PRT
<213> ORGANISM: Artificial Sequence
<220> FEATURE:
<223> OTHER INFORMATION: Peptide Substrate

<400> SEQUENCE: 8

Lys Arg Arg Arg Ala Leu Ser Val Ala Ser Leu Pro Gly Leu
1               5                   10

<210> SEQ ID NO 9
<211> LENGTH: 23
<212> TYPE: PRT
<213> ORGANISM: Artificial Sequence
<220> FEATURE:
<223> OTHER INFORMATION: Peptide Substrate

<400> SEQUENCE: 9

Lys Lys Lys Lys Glu Arg Leu Leu Asp Asp Arg His Asp Ser Gly Leu
1               5                   10                  15

Asp Ser Met Lys Asp Glu Glu
            20

<210> SEQ ID NO 10
```

```
<211> LENGTH: 21
<212> TYPE: PRT
<213> ORGANISM: Artificial Sequence
<220> FEATURE:
<223> OTHER INFORMATION: Peptide Substrate

<400> SEQUENCE: 10

Arg Arg Glu Leu Val Glu Pro Leu Thr Pro Ser Gly Glu Ala Pro Asn
1               5                   10                  15

Gln Ala Leu Leu Arg
            20

<210> SEQ ID NO 11
<211> LENGTH: 13
<212> TYPE: PRT
<213> ORGANISM: Artificial Sequence
<220> FEATURE:
<223> OTHER INFORMATION: Peptide Substrate

<400> SEQUENCE: 11

Lys Lys Leu Asn Arg Thr Leu Ser Phe Ala Glu Pro Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Peptide Substrate

<400> SEQUENCE: 12

Gly Arg Pro Arg Thr Ser Ser Phe Ala Glu Gly Lys Lys
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Peptide Substrate

<400> SEQUENCE: 13

Lys Glu Ala Lys Glu Lys Arg Gln Glu Gln Ile Ala Lys Arg Arg Arg
1               5                   10                  15

Leu Ser Ser Leu Arg Ala Ser Thr Ser Lys Ser Gly Gly Ser Gln Lys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Peptide Substrate

<400> SEQUENCE: 14

Arg Ser Arg His Ser Ser Tyr Pro Ala Gly Thr
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Peptide Substrate

<400> SEQUENCE: 15
```

```
Glu Arg Met Arg Pro Arg Lys Arg Gln Gly Ser Val Arg Arg Val
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: Peptide Substrate

<400> SEQUENCE: 16

Ala Lys Arg Arg Arg Leu Ser Ser Leu Arg Ala
1               5                   10
```